(12) United States Patent
Smith

(10) Patent No.: US 10,874,429 B2
(45) Date of Patent: Dec. 29, 2020

(54) SURGICAL ACCESS DEVICE INCLUDING GIMBAL MOUNT COOPERATING WITH BELLOWS ATTACHED TO PROXIMAL WALL OF SEAL HOUSING

(71) Applicant: Covidien LP, Mansfield, MA (US)

(72) Inventor: Robert C. Smith, Chapin, SC (US)

(73) Assignee: COVIDIEN LP, Mansfield, MA (US)

( * ) Notice: Subject to any disclaimer, the term of this patent is extended or adjusted under 35 U.S.C. 154(b) by 231 days.

(21) Appl. No.: 15/897,302

(22) Filed: Feb. 15, 2018

(65) Prior Publication Data

US 2018/0168685 A1    Jun. 21, 2018

Related U.S. Application Data

(63) Continuation of application No. 14/156,530, filed on Jan. 16, 2014, now Pat. No. 9,901,372.

(60) Provisional application No. 61/767,358, filed on Feb. 21, 2013.

(51) Int. Cl.
   *A61B 17/34*        (2006.01)

(52) U.S. Cl.
   CPC ...... *A61B 17/3462* (2013.01); *A61B 17/3474* (2013.01)

(58) Field of Classification Search
   CPC ..... A61B 2017/3423; A61B 2017/3425–3427; A61B 17/3423
   See application file for complete search history.

(56) References Cited

U.S. PATENT DOCUMENTS

| 5,342,315 | A  | 8/1994  | Rowe et al.   |
|-----------|----|---------|---------------|
| 5,720,759 | A  | 2/1998  | Green et al.  |
| 5,989,224 | A  | 11/1999 | Exline et al. |
| 7,582,071 | B2 | 9/2009  | Wenchell      |
| 7,632,250 | B2 | 12/2009 | Smith et al.  |
| 7,896,847 | B2 | 3/2011  | Wenchell      |

(Continued)

FOREIGN PATENT DOCUMENTS

| EP | 0638290 A1 | 2/1995 |
|----|------------|--------|
| EP | 2229897 A1 | 9/2010 |

(Continued)

OTHER PUBLICATIONS

Extended European Search Report dated Sep. 19, 2013 for EP 13 16 7615.

(Continued)

*Primary Examiner* — Olivia C Chang
(74) *Attorney, Agent, or Firm* — Carter, DeLuca & Farrell LLP

(57) ABSTRACT

A surgical access device includes a seal assembly having a seal housing and a gimbal mount disposed within the seal housing, the seal housing defining a central longitudinal axis and having a longitudinal passage for receiving at least one surgical object therethrough and the gimbal mount adapted for angular movement relative to the central longitudinal axis. The seal assembly also includes a bellows configured to engage at least a portion of the gimbal mount, the bellows dimensioned and adapted to establish a biasing relationship with the gimbal mount, such that the bellows biases the gimbal mount to align with the central longitudinal axis of the seal housing. The bellows is configured to be attached to a proximal wall of the seal housing.

15 Claims, 21 Drawing Sheets

(56) References Cited

U.S. PATENT DOCUMENTS

| | | |
|---|---|---|
| 7,931,624 B2 | 4/2011 | Smith et al. |
| 7,951,118 B2 | 5/2011 | Smith et al. |
| 8,357,085 B2 | 1/2013 | Shelton, IV et al. |
| 9,901,372 B2 | 2/2018 | Smith |
| 2004/0066008 A1 | 4/2004 | Smith |
| 2004/0068232 A1 | 4/2004 | Hart et al. |
| 2004/0204682 A1 | 10/2004 | Smith |
| 2006/0224164 A1* | 10/2006 | Hart .................. A61B 17/3462 606/108 |
| 2007/0088277 A1 | 4/2007 | McGinley et al. |
| 2007/0255218 A1 | 11/2007 | Franer |
| 2008/0125716 A1 | 5/2008 | Cruz |
| 2010/0049138 A1 | 2/2010 | Smith et al. |
| 2011/0124972 A1 | 5/2011 | Wenchell |
| 2011/0196207 A1 | 8/2011 | Smith et al. |
| 2011/0201891 A1 | 8/2011 | Smith et al. |
| 2013/0310773 A1 | 11/2013 | Richard et al. |

FOREIGN PATENT DOCUMENTS

| | | |
|---|---|---|
| EP | 2233090 A1 | 9/2010 |
| GB | 2287760 A | 9/1995 |
| WO | 9742991 A1 | 11/1997 |
| WO | 9952577 A1 | 10/1999 |
| WO | 03094760 A2 | 11/2003 |
| WO | 2007121425 A1 | 10/2007 |

OTHER PUBLICATIONS

Extended European Search Report dated Jun. 14, 2013 for EP 13 16 7618.

* cited by examiner

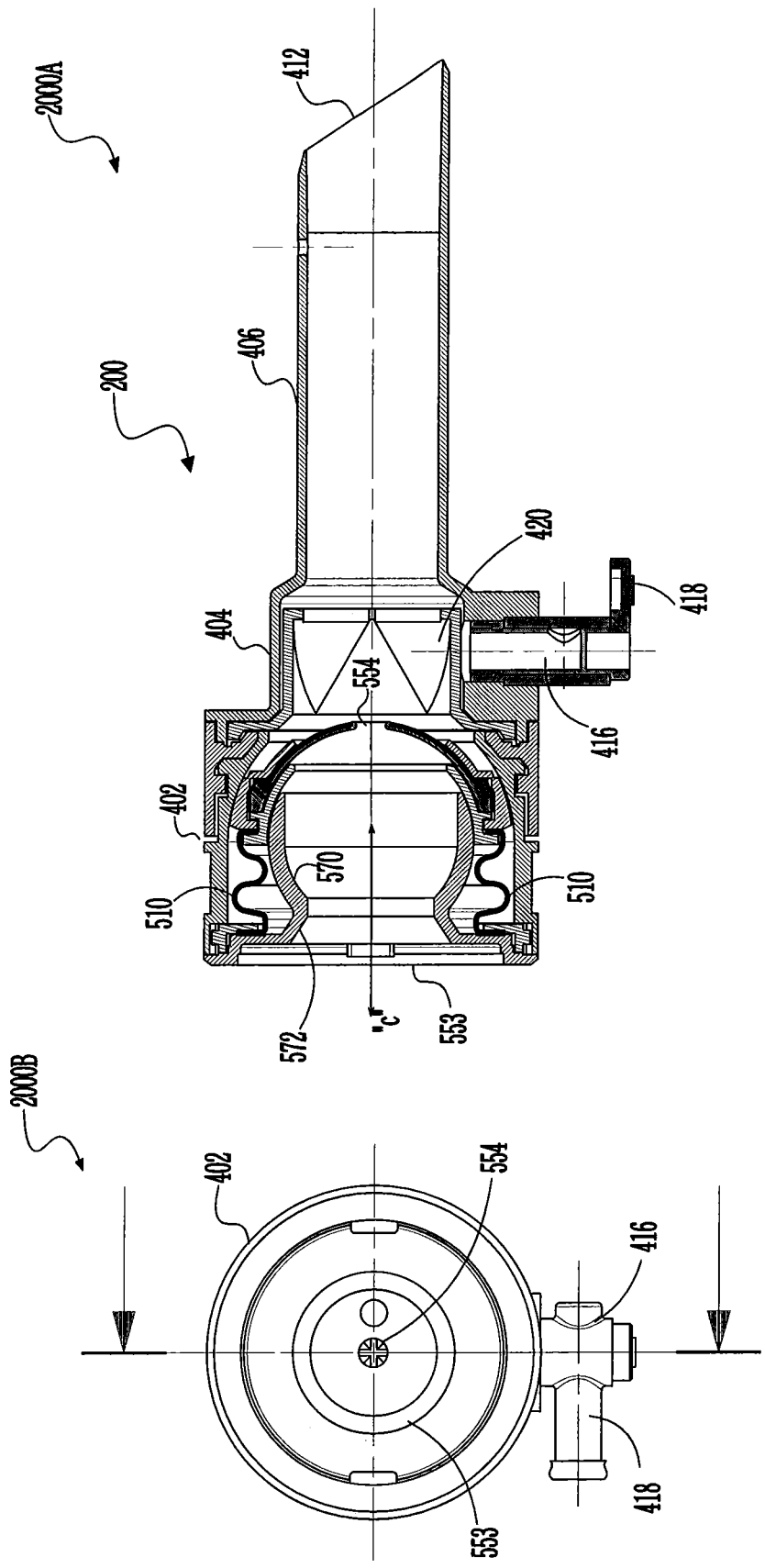

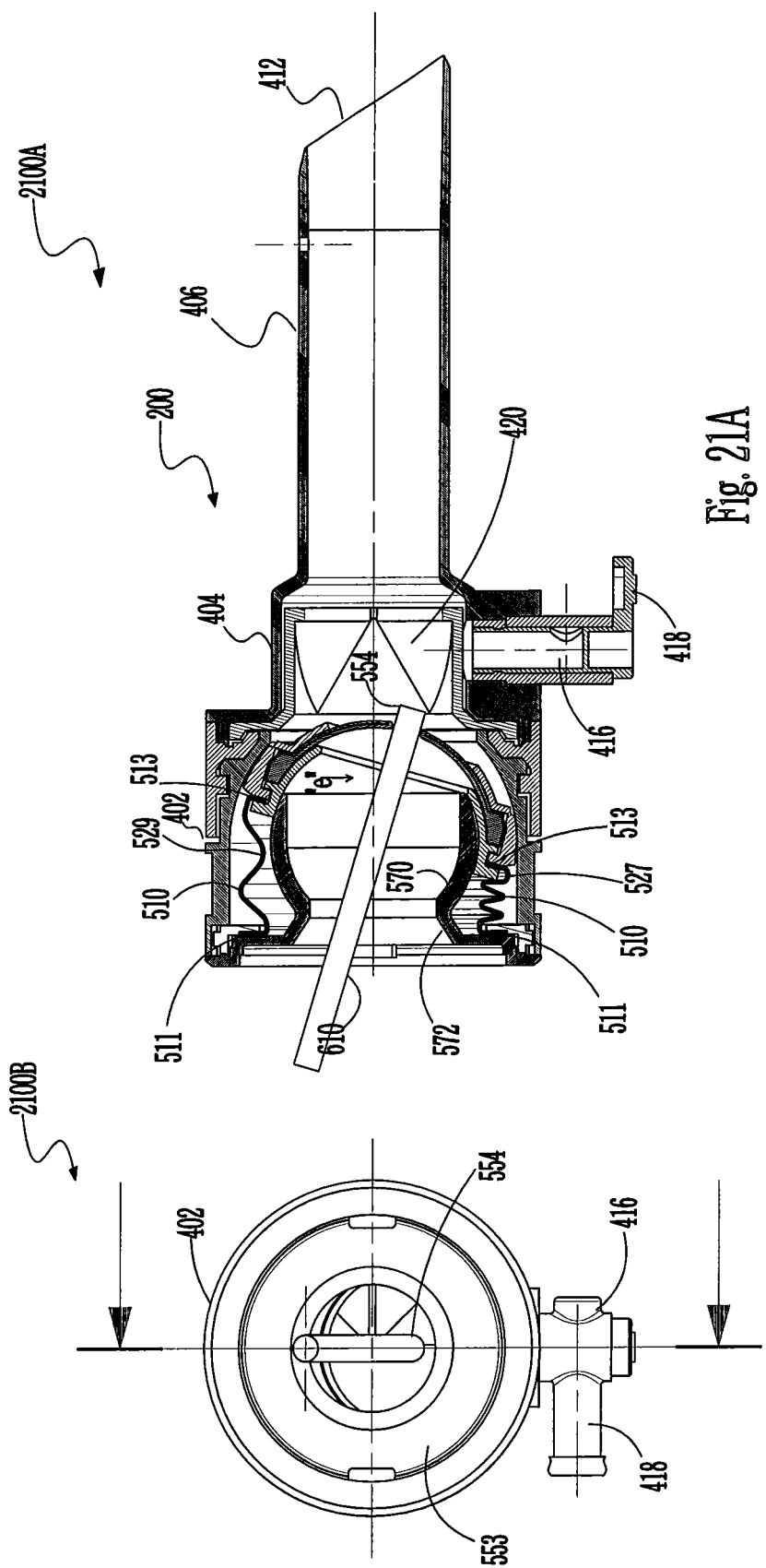

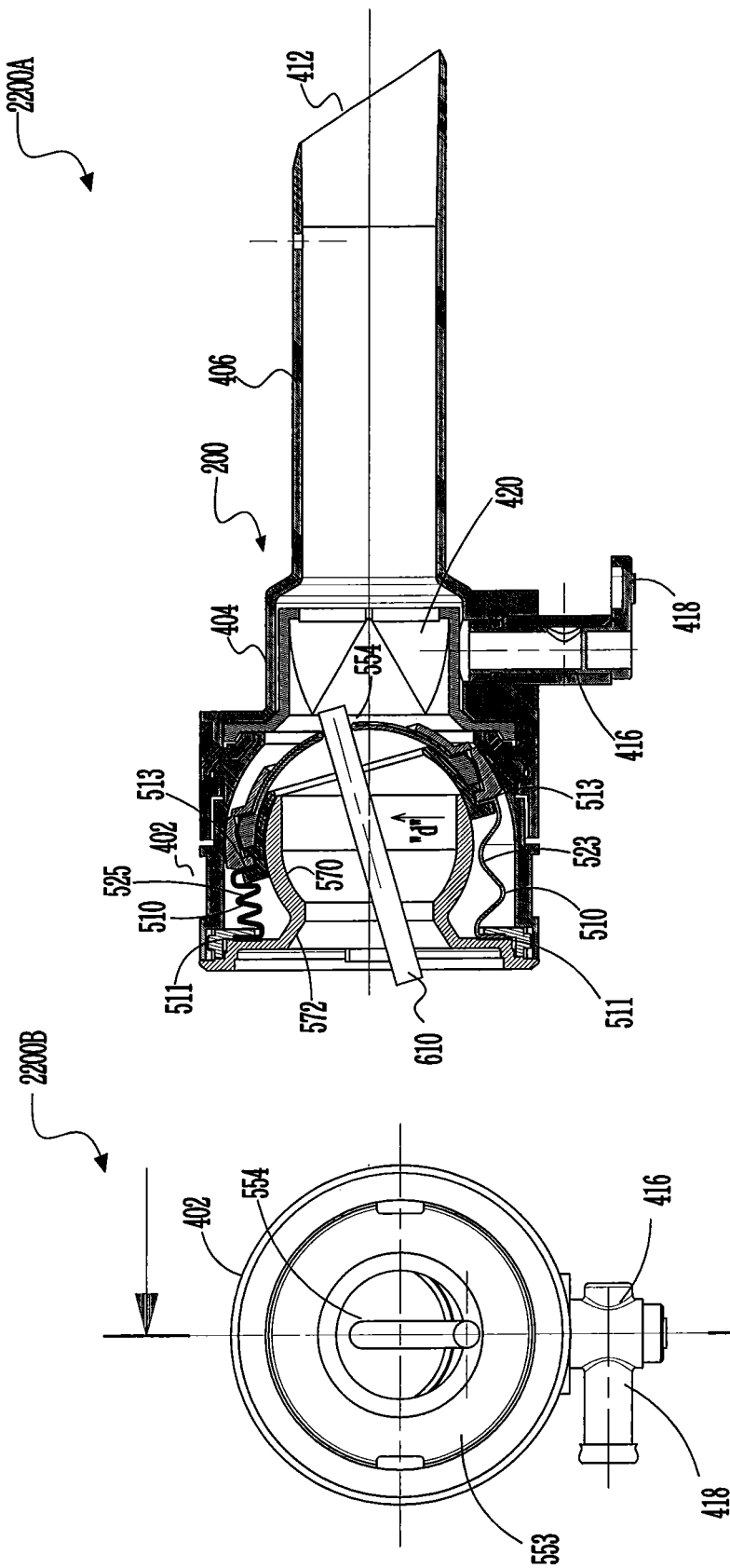

SURGICAL ACCESS DEVICE INCLUDING GIMBAL MOUNT COOPERATING WITH BELLOWS ATTACHED TO PROXIMAL WALL OF SEAL HOUSING

CROSS-REFERENCE TO RELATED APPLICATIONS

This is a continuation of U.S. patent application Ser. No. 14/156,530, filed Jan. 16, 2014, which claims the benefit of and priority to U.S. Provisional Patent Application No. 61/767,358, filed Feb. 21, 2013, the entire disclosure of which is incorporated by reference herein.

BACKGROUND

Technical Field

The present disclosure relates to a seal system adapted to permit the introduction of surgical instrumentation into a patient's body. In particular, the present disclosure relates to a seal system for use with an introducer or access device, which is intended for insertion into a patient's body, and to receive an instrument in sealing engagement therewith.

Background of Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere.

In view of the need to maintain the atmospheric integrity of the inner area of the cavity, a seal assembly for a cannula, which permits introduction of a wide range of surgical instrumentation and maintains the atmospheric integrity of the inner area of the cavity, is desirable. In this regard, there have been a number of attempts in the prior art to achieve such sealing requirements. A difficulty encountered with conventional seal assemblies, however, is the inability of accommodating the wide range of sizes of instrumentation. In addition, angulation and/or manipulation of instrumentation within the cannula often present difficulties with respect to maintaining seal integrity.

SUMMARY

According to one aspect of the present disclosure, a surgical access device is provided. The surgical access device includes a seal assembly including a seal housing and a gimbal mount disposed within the seal housing, the seal housing defining a central longitudinal axis and having a longitudinal passage for receiving at least one surgical object therethrough and the gimbal mount adapted for angular movement relative to the central longitudinal axis. The seal assembly also includes a bellows configured to engage at least a portion of the gimbal mount, the bellows dimensioned and adapted to establish a biasing relationship with the gimbal mount, such that the bellows biases the gimbal mount to align with the central longitudinal axis of the seal housing. The bellows is configured to be attached to a proximal wall of the seal housing.

In previous seal arrangements, when a movable valve is in a position in which its longitudinal passage is misaligned with the central longitudinal axis, friction that exists between the valve, e.g., a gimbal mount, and the seal housing causes the longitudinal passage of the valve to be out of alignment with the central longitudinal axis. When this occurs, insertion of instruments through the valve is more likely to tear or otherwise damage the valve, because the sharp tip of such an instrument engages the elastomeric material adjacent to the passage, rather than passing directly through the passage, or else engages the elastomeric material too far from the passage such that the valve is unable to move sufficiently before being torn. By biasing the longitudinal passage of the seal assembly towards the central longitudinal axis, the bellows overcomes the frictional relationship that exists between the gimbal mount and the seal housing, and thereby may decrease the likelihood that the gimbal mount will be damaged during use. In addition, the use of a bellows provides an additional sealing benefit, as insufflation gas is not permitted by the bellows from escaping between the gimbal mount and the seal housing. Attaching the bellows to the proximal wall of the seal housing also decreases or eliminates the need for additional spacing within the seal housing in a location proximal to the gimbal mount, thereby enabling the height of the seal housing to be reduced. Still further, the bellows provides a relatively small amount of biasing force to the gimbal mount—such a small force may be advantageous when a surgeon is using the device. More specifically, the bellows provides for a biasing force that is large enough to enable the benefits of self-centering the gimbal mount, but small enough such that manipulation of an instrument within the seal won't cause the passage of the seal to become "cat-eyed" or stretched to a degree that would cause leakage.

In one exemplary embodiment, the gimbal mount defines a substantially parabolic configuration.

In yet another exemplary embodiment, the seal assembly includes an upper housing portion and a lower housing portion, the upper housing portion mechanically cooperating with the bellows such that the bellows is circumferentially adjacent the longitudinal passage of the seal housing.

In another exemplary embodiment, the upper housing portion defines an angular opening therethrough to facilitate angular reception of the at least one surgical object.

Additionally, the bellows is dimensioned and adapted to inhibit passage of fluids through the seal housing. The bellows may have a uniform wall thickness of about 0.01 inches.

In one exemplary embodiment, the bellows extends to the proximal wall of the seal housing in parallel to the central longitudinal axis defined through the seal housing.

In another exemplary embodiment, the bellows is positioned within a space such that the gimbal mount is movable relative to the seal housing, the space defined between an inner wall and an outer wall of the seal housing.

In yet another exemplary embodiment, one side of the bellows expands and another side of the bellows contracts as the at least one surgical instrument in inserted through and maneuvered within the longitudinal passage of the seal housing.

In an alternative embodiment, the bellows connects to the gimbal mount to form a single integral unit.

In another aspect of the present disclosure, a cannula assembly is provided. The cannula assembly includes a cannula housing, a cannula sleeve extending distally from the cannula housing and a seal assembly disposed in mechanical cooperation with the cannula housing. The seal assembly includes a seal assembly including a seal housing and a gimbal mount disposed within the seal housing, the seal housing defining a central longitudinal axis and having a longitudinal passage for receiving at least one surgical object therethrough and the gimbal mount adapted for angular movement relative to the central longitudinal axis. The seal assembly also includes a bellows configured to engage at least a portion of the gimbal mount, the bellows dimensioned and adapted to establish a biasing relationship with the gimbal mount, such that the bellows biases the gimbal mount to align with the central longitudinal axis of the seal housing. The bellows is configured to be attached to a proximal wall of the seal housing.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 20A is a side cross-sectional view of the cannula and seal assemblies, illustrating the gimbal mount connected to the bellows, in accordance with the embodiments of the present disclosure;

FIG. 20B is a top view of the cannula and seal assembly of FIG. 20A;

FIG. 21A is a side cross-sectional view of the cannula and seal assemblies illustrating a range of movement of the surgical instrument inserted through the gimbal mount, where the instrument moves to the left to expand/contract the bellows, in accordance with the embodiments of the present disclosure;

FIG. 21B is a top view of the cannula assembly of FIG. 21A;

FIG. 22A is a side cross-sectional view of the cannula and seal assemblies illustrating a range of movement of the surgical instrument inserted through the gimbal mount, where the instrument moves to the right, to contract expand the bellows, in accordance with the embodiments of the present disclosure;

FIG. 22B is a top view of the cannula assembly of FIG. 22A;

Figure 1:
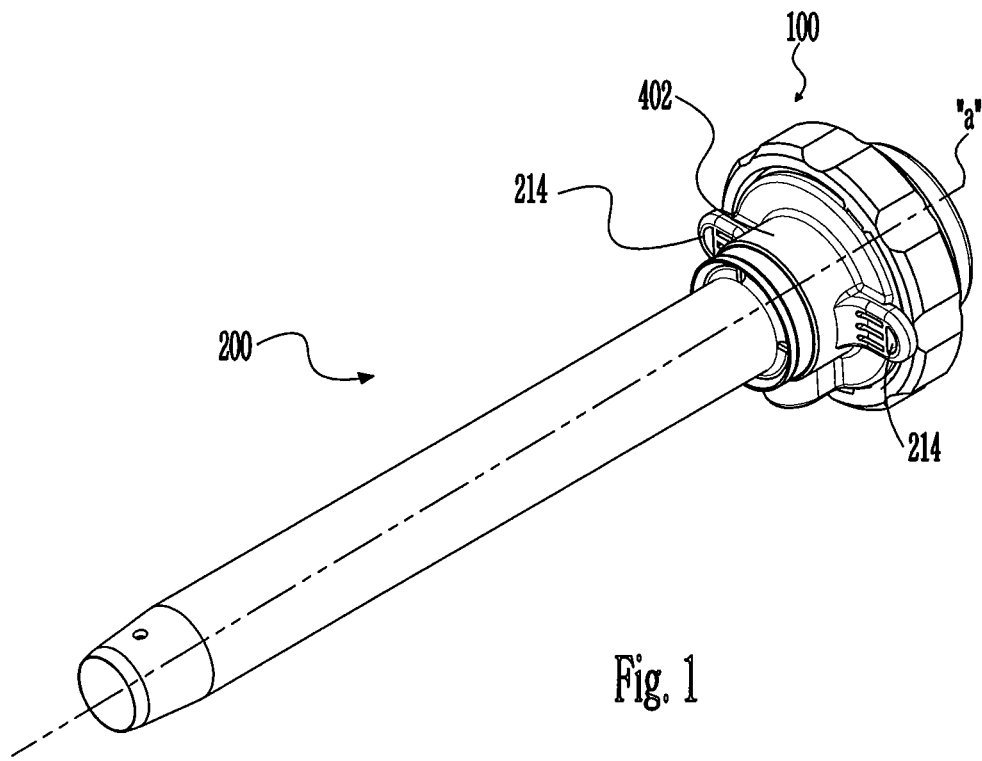
FIGS. 1-2 are perspective views of a cannula assembly and a seal assembly.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Particular embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The seal assembly of the present disclosure, either alone or in combination with a seal system internal to a cannula assembly, provides a substantial seal between a body cavity of a patient and the outside atmosphere before, during and after insertion of an instrument through the cannula assembly. Moreover, the seal assembly of the present disclosure is capable of accommodating instruments of varying diameters, e.g., from 5 mm to 15 mm, by providing a fluid tight seal with each instrument when inserted. The flexibility of the present seal assembly greatly facilitates endoscopic surgery where a variety of instruments having differing diameters are often needed during a single surgical procedure.

The seal assembly contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. Specifically, the seal assembly accommodates angular manipulation of the surgical instrument relative to the seal housing axis. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation."

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Figure 2:
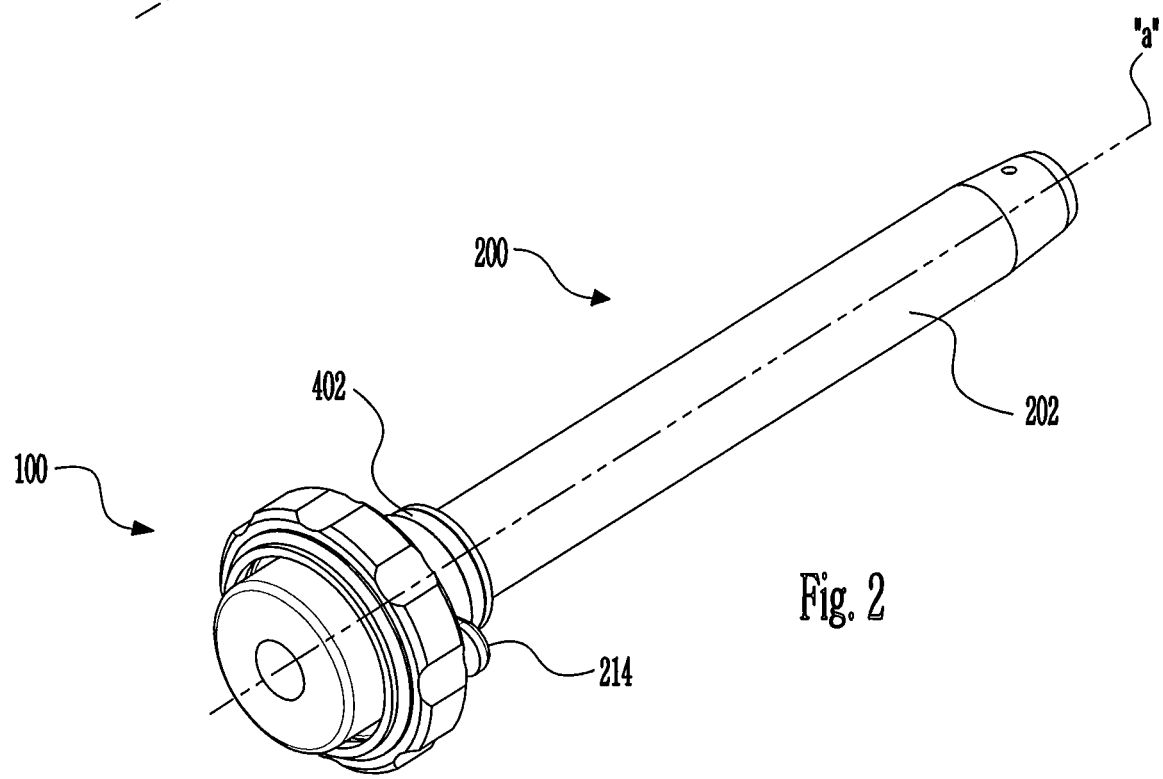

Referring now to the drawings, in which like reference numerals identify identical or substantially similar parts throughout the several views, FIGS. 1-2 illustrate the seal assembly 100 of the present disclosure mounted to cannula assembly 200. Cannula assembly 200 may be any conventional cannula suitable for the intended purpose of accessing a body cavity and permitting introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown), which is a sharp pointed instrument positionable within the passageway of the cannula assembly 200. The obturator assembly is utilized to penetrate the abdominal wall and then subsequently be removed from the cannula assembly 200 to permit introduction of the surgical instrumentation utilized to perform the procedure.

Cannula assembly 200 includes cannula sleeve 202 and cannula housing 402 mounted to an end of the sleeve 202. Cannula sleeve 202 defines a longitudinal axis "a" extending along the length of sleeve 202. Sleeve 202 further defines an internal longitudinal passage dimensioned to permit passage of surgical instrumentation. Sleeve 202 may be formed of stainless steel or other rigid materials, such as a polymeric material or the like. Sleeve 202 may be clear or opaque. The diameter of sleeve 202 may vary, but typically ranges from 10 to 15 mm for use with the seal assembly 100 of the present disclosure.

Figure 3:
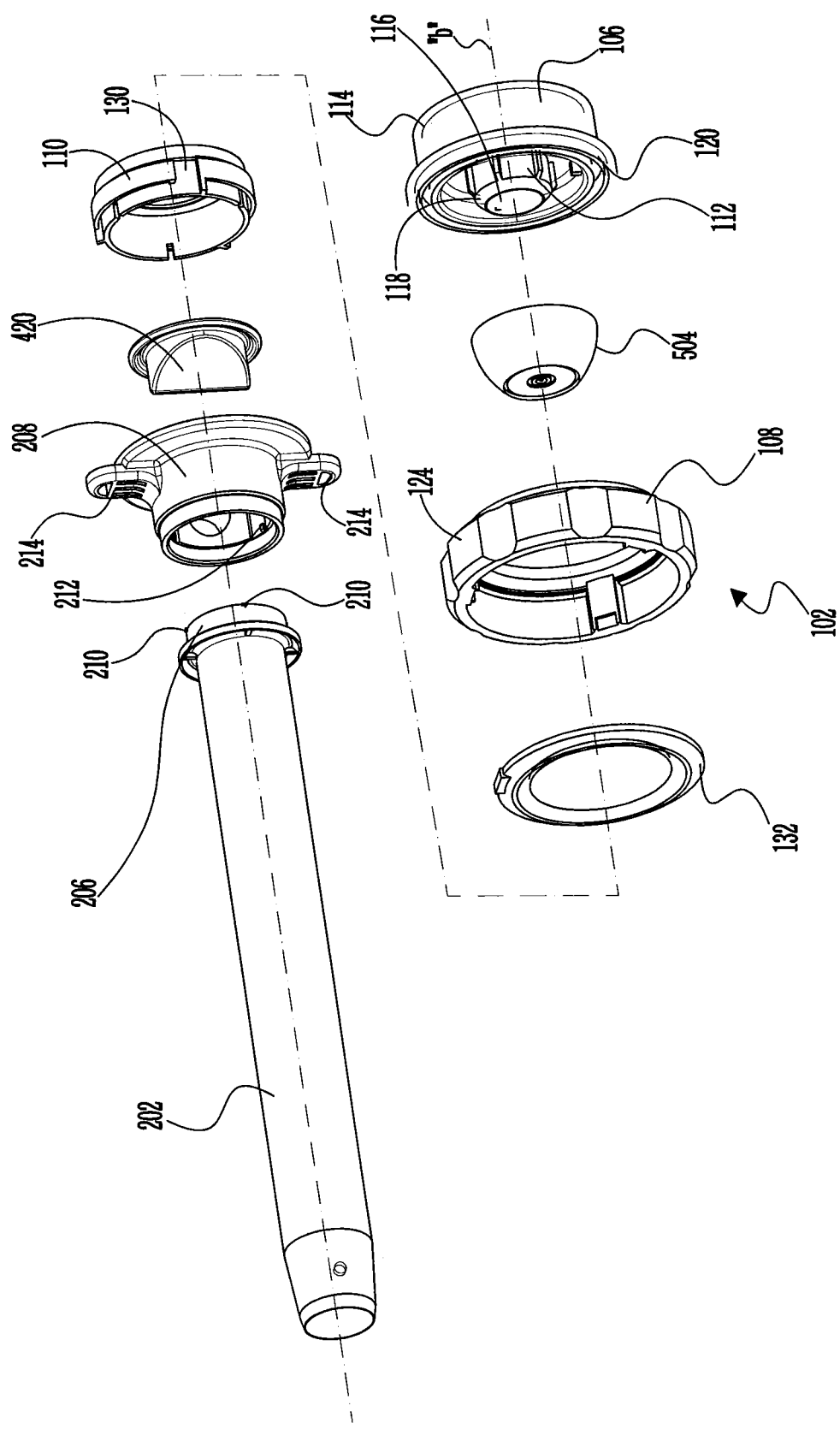
FIG. 3 is a perspective view, with parts separated, of the cannula and seal assemblies of FIGS. 1-2.

Cannula housing 402 includes two components, specifically, housing flange 206 (see FIG. 3), which is attached to the proximal end of cannula sleeve 202 and main housing 208, as shown in FIG. 3. Main housing 208 is connectable to housing flange 206 through a bayonet coupling consisting of radially spaced tongues 210 on the exterior of housing flange 206 and corresponding recesses 212 within the interior of main housing 208. Tongues 210 are receivable within recesses 212. Thereafter, housing flange 206 and main housing 208 are rotated to securely lock the tongues 210 within the recesses 212. Other conventional means, e.g., a snap fit, ultrasonic welding or any other means envisioned by one skilled in the art including, e.g., adhesive means, may be incorporated to connect housing flange 206 and main housing 208. Main housing 208 further includes diametrically opposed housing grips 214 dimensioned and arranged for gripping engagement by the fingers of the user.

With reference to FIG. 3, in conjunction with FIGS. 1-2, cannula housing 402 further includes duck bill or zero closure valve 420, which tapers distally and inwardly to a sealed configuration. Valve 420 opens to permit passage of the surgical instrumentation and closes in the absence of the instrumentation. Valve 420 is preferably adapted to close upon exposure to the forces exerted by the insufflation gases in the internal cavity. Other zero closure valves are also contemplated including single or multiple slit valve arrangements, trumpet valves, flapper valves, etc.

Referring again to FIG. 3, in conjunction with FIGS. 1-2, seal assembly 100 will be discussed in detail. Seal assembly 100 includes seal housing, generally identified as reference numeral 102, and gimbal mount 504, which is disposed within the seal housing 102. Seal housing 102 houses the sealing components of the assembly and defines the outer valve or seal body of the seal assembly 100. Seal housing 102 defines central seal housing axis "b," which is preferably coaxial to the axis "a" of cannula sleeve 202 and, more specifically, coincident with the axis "a" of the cannula.

Seal housing 102 incorporates three housing components, namely, proximal, distal and lower housing components 106, 108, 110, respectively, which, when assembled together, form the seal housing 102. The proximal lower housing component 106 may also be referred to as the "upper housing portion," whereas the distal lower housing components 108, 110 may also be referred to as "lower housing portions." Assembly of housing components 106, 108, 110 may be affected by any of the aforementioned connection means discussed with respect to cannula housing 402. Therefore, seal housing 102 may be considered as having an upper housing portion formed by component 106, and a detachable lower housing portion formed by components 108, 110.

Proximal housing component 106 defines inner guide wall 112 and outer wall 114 disposed radially outwardly of the inner guide wall 112. Inner guide wall 112 defines central passage 116, which is dimensioned to receive a surgical instrument and laterally confine the instrument within seal housing 102. Inner guide wall 112 is generally cylindrical in configuration and terminates in a distal arcuate surface 118. Outer wall 114 defines an annular recess 120 adjacent its distal end. Recess 120 receives radially spaced tongues (see FIGS. 3 and 18) of distal housing component 108 to facilitate connection of the two components. As appreciated, proximal housing component 106 may also incorporate locking tabs, which engage corresponding structure of distal housing component 108 upon relative rotation of the components 106, 108 to securely connect the components.

Lower housing component 110 is disposed within the interior of distal housing component 108 and is securely connectable to the distal housing component 108 through a bayonet coupling. Such coupling includes radially spaced tongues 124, which depend radially inwardly to be received within correspondingly arranged grooves or recesses 130 on the exterior of lower housing component 110. Coupling of distal and lower housing components 108, 110 is thereby affected through simple rotation of the components.

Seal assembly 100 may be associated with, or joined to, cannula assembly 200 in a variety of ways. In a preferred embodiment, seal housing 102 of seal assembly 100 and cannula housing 402 of cannula assembly 200 are adapted to detachably engage each other, e.g., through a bayonet lock or like mechanical means. As previously discussed, proximal and distal housing components 106, 108 may define an upper housing component 109 (see FIGS. 15-17), which is mountable directly to cannula assembly 200. Alternatively, inner housing portion 110 which defines a lower housing component may be directly mounted to cannula assembly 200 independent of the upper housing component 109. Specifically, the lower housing component 110 which houses gimbal mount 504 may be mounted to cannula assembly independent of the remaining housing components. The upper housing may then be mounted to lower housing or cannula assembly 200 as needed. Even further, upper housing component 109 may be mounted to cannula assembly 200 without lower housing component 110. Other means of joining seal assembly 100 to cannula assembly 200 will be readily apparent to one of ordinary skill in the art.

With continued reference to FIG. 3, seal assembly 100 further includes skirt seal 132 mounted about the proximal end of lower housing component 110 or on the upper surface of the lower housing component of the seal housing 102. Skirt seal 132 functions in minimizing the loss of insufflation gases through seal assembly 100. Stated differently, skirt seal 132 is adapted to inhibit passage of fluids through seal assembly 100. Skirt seal 132 also engages gimbal mount 504 and serves to bias the gimbal mount 504 in a proximal direction against inner guide wall 112 of proximal housing 106. Gimbal mount 504 is configured to rotate about central longitudinal axis "a" independent of the skirt seal 132. Additionally, skirt seal 132 may include an inner circumferential edge configured to slidably engage skirt seal 132. Skirt seal 132 is preferably fabricated from a suitable elastomeric material or the like to provide a spring-like characteristic sufficient to appropriately bias gimbal mount 504.

Figure 4:
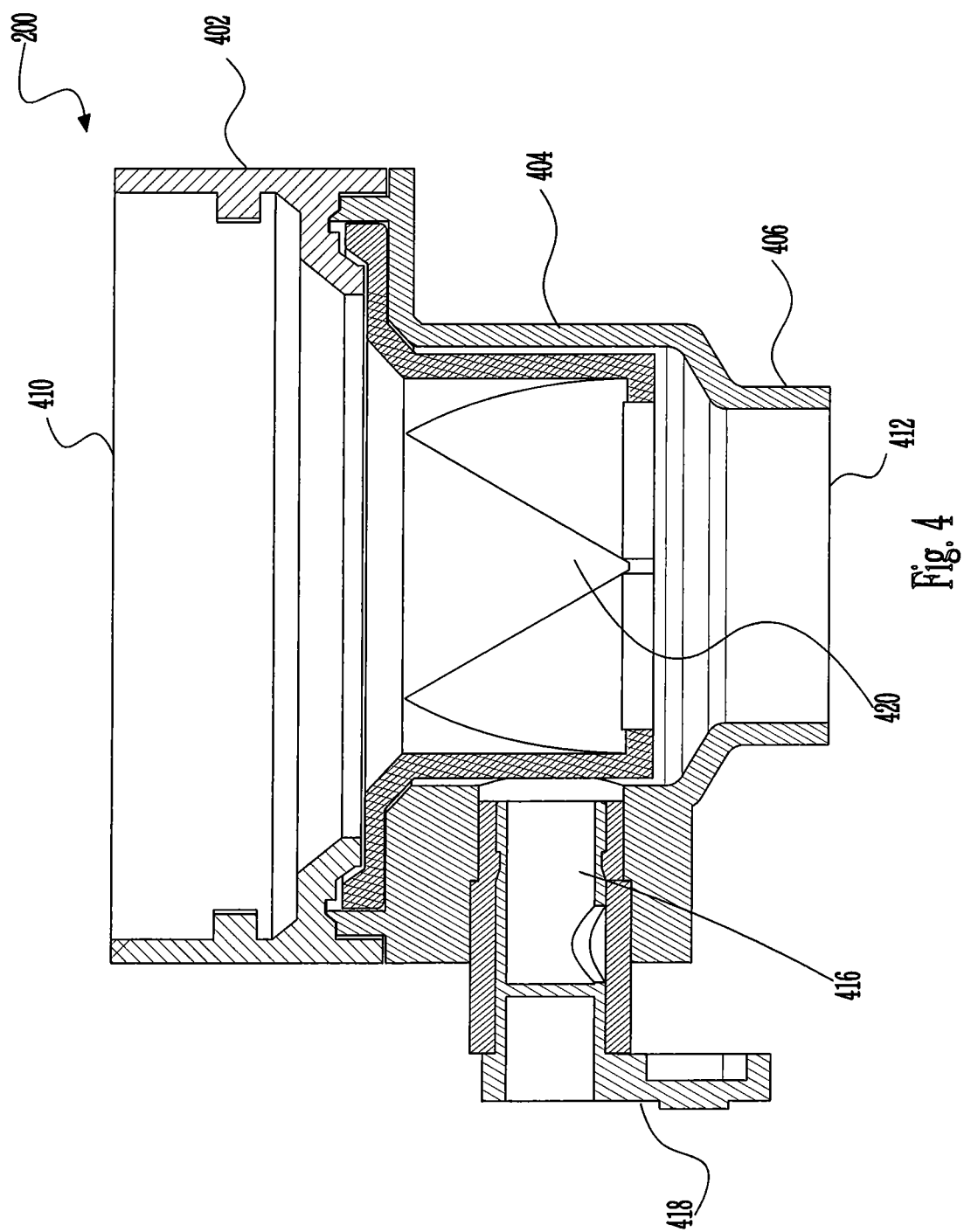
FIG. 4 is a side cross-sectional view of a portion of a cannula assembly, in accordance with an embodiment of the present disclosure.

Referring to FIG. 4, a side cross-sectional view of a portion of a cannula assembly 200, in accordance with an embodiment of the present disclosure is presented.

The cannula assembly 200 includes an upper cannula housing 402 and a lower cannula housing 404 connected thereto. The lower cannula housing 404 is connected to a cannula sleeve 406 that extends distally from the lower cannula housing 404. The cannula assembly 200 includes an opening 410 at the upper cannula housing 402 for receiving surgical instrumentation therethrough. The cannula sleeve 406 includes an opening 412 at a distal end thereof where the surgical instrumentation exits into, for example, a body cavity of a patient. The lower cannula housing 404 may include a duck bill seal 420 therein, which tapers distally and inwardly to a sealed configuration. Moreover, lower cannula housing 404 may include a luer fitting 416 positioned within a port opening. Luer fitting 416 is adapted for connection to a supply of insufflation gas and incorporates valve 418 to selectively open and close the passage of luer fitting 416.

Figure 5:
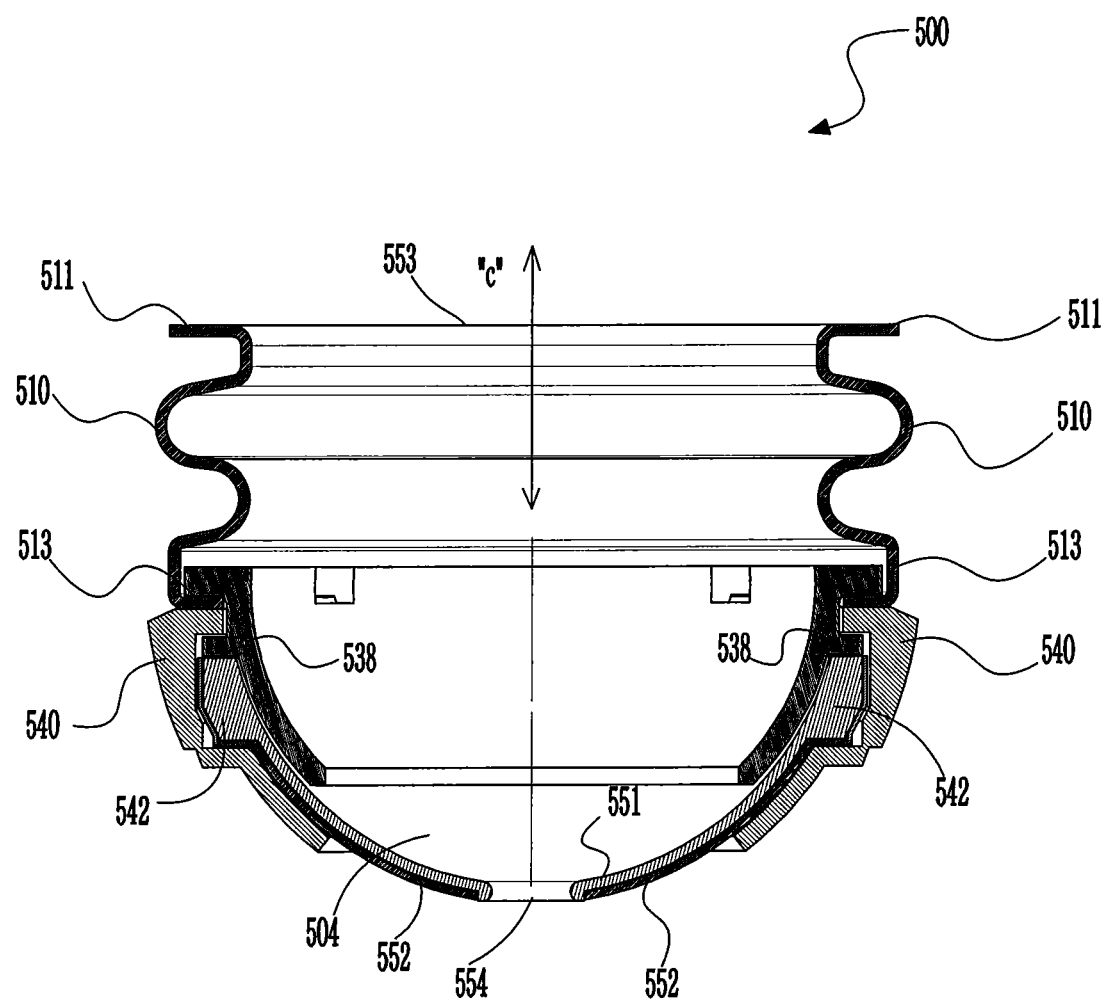
FIG. 5 is a side cross-sectional view of the bellows attached to the gimbal mount, in accordance with an embodiment of the present disclosure.

Referring to FIG. 5, a side cross-sectional view 500 of the bellows 510 attached to the gimbal mount 504, in accordance with an embodiment of the present disclosure is presented Gimbal mount 504 includes first and second gimbal housings 538, 540 and resilient seal member 542, which is mounted between the housings 538, 540. In a preferred arrangement, first and second gimbal housings 538, 540 and seal member 542 each define a substantially hemispherical configuration. However, one skilled in the art may contemplate a gimbal mount 504 defining a substantially parabolic configuration. First gimbal housing 538 is preferably seated within second gimbal housing 540 and secured to the second gimbal housing 540 through a snap fit connection or the like.

Seal member 542 of gimbal mount 504 is secured in interposed relation between first and second gimbal housings 538, 540. Seal member 542 preferably comprises a resilient center material (e.g., polyisoprene or natural rubber) with first and second layers of fabric 551, 552 impregnated on the respective proximal and distal surfaces of the resilient center material.

Seal member 542 defines central aperture 554 for sealed reception of a surgical instrument (see FIGS. 7, 8, 9A, and 9B). In a preferred arrangement, first layer 551 is arranged to extend or overlap into aperture 554. In this manner, the fabric (which is stronger relative to the resilient material) is positioned to engage the surgical instrument upon passage through aperture 554 of seal member 542 thereby protecting the resilient material defining the aperture 554. This advantageously minimizes the potential of piercing, penetrating or tearing of the resilient material by the instrument.

Referring to the bellows 510, a second end 513 of bellows 510 is secured in interposed relation between first and second gimbal housings 538, 540. The bellows 510 includes a first end 511 and a second end 513. The bellows 510 is attached or connected to a proximal wall or top wall of the upper cannula housing 402, as will be discussed in detail below. Bellows 510 is shown as a non-linear bellows. However, one skilled in the art may contemplate a plurality of different shapes and sizes for bellows 510. Bellows 510 also includes an opening 553 for receiving surgical instrumentation, as will be discussed in further detail below.

Gimbal mount 504 is free to move and is in cooperation with bellows 510 to permit angulation of the instrument relative to the seal axis "c," while still maintaining a seal thereabout.

Figure 6:
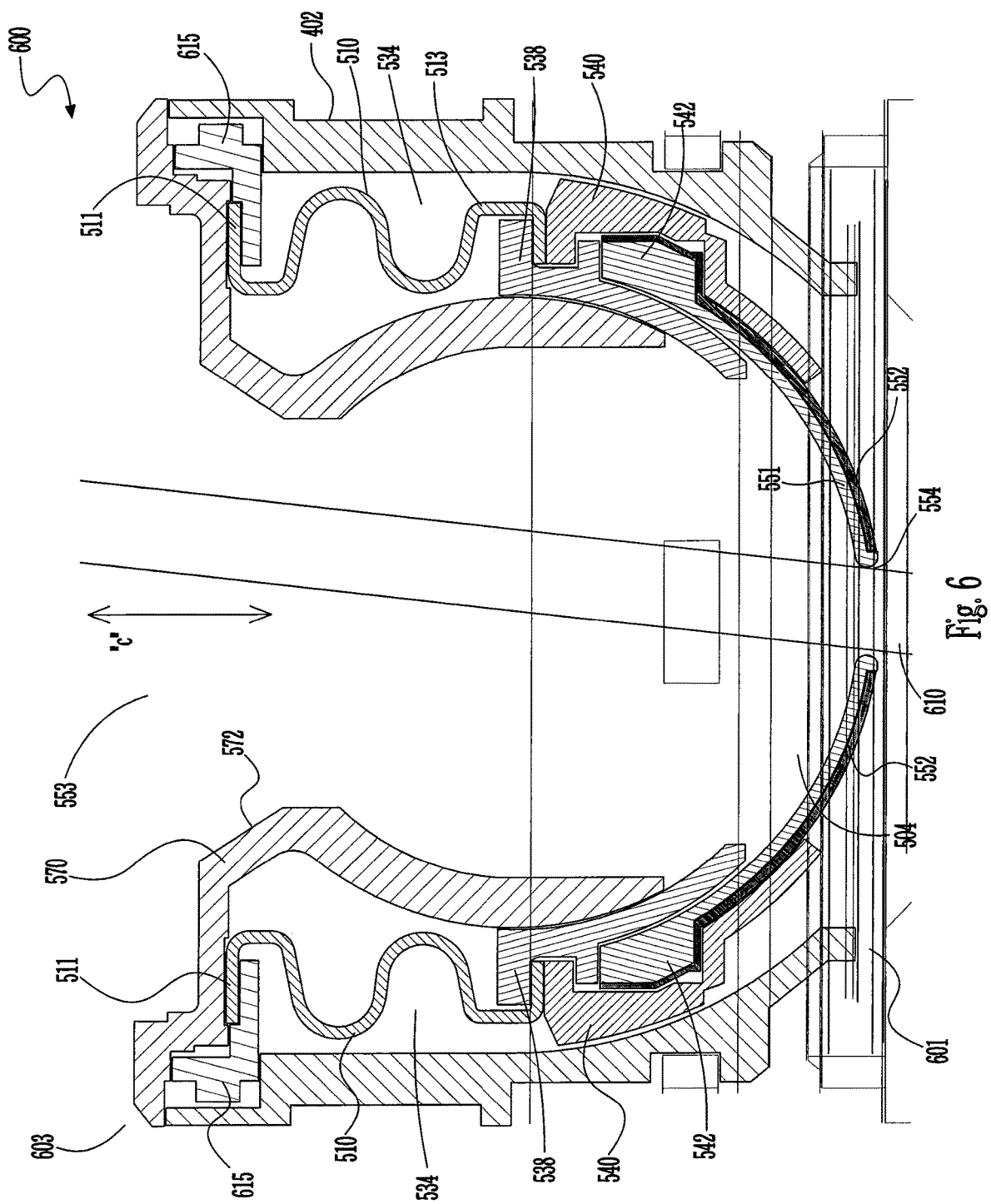
FIG. 6 illustrates a side cross-sectional view of the bellows and gimbal mount positioned within the seal housing, in accordance with an embodiment of the present disclosure.
Figure 7:
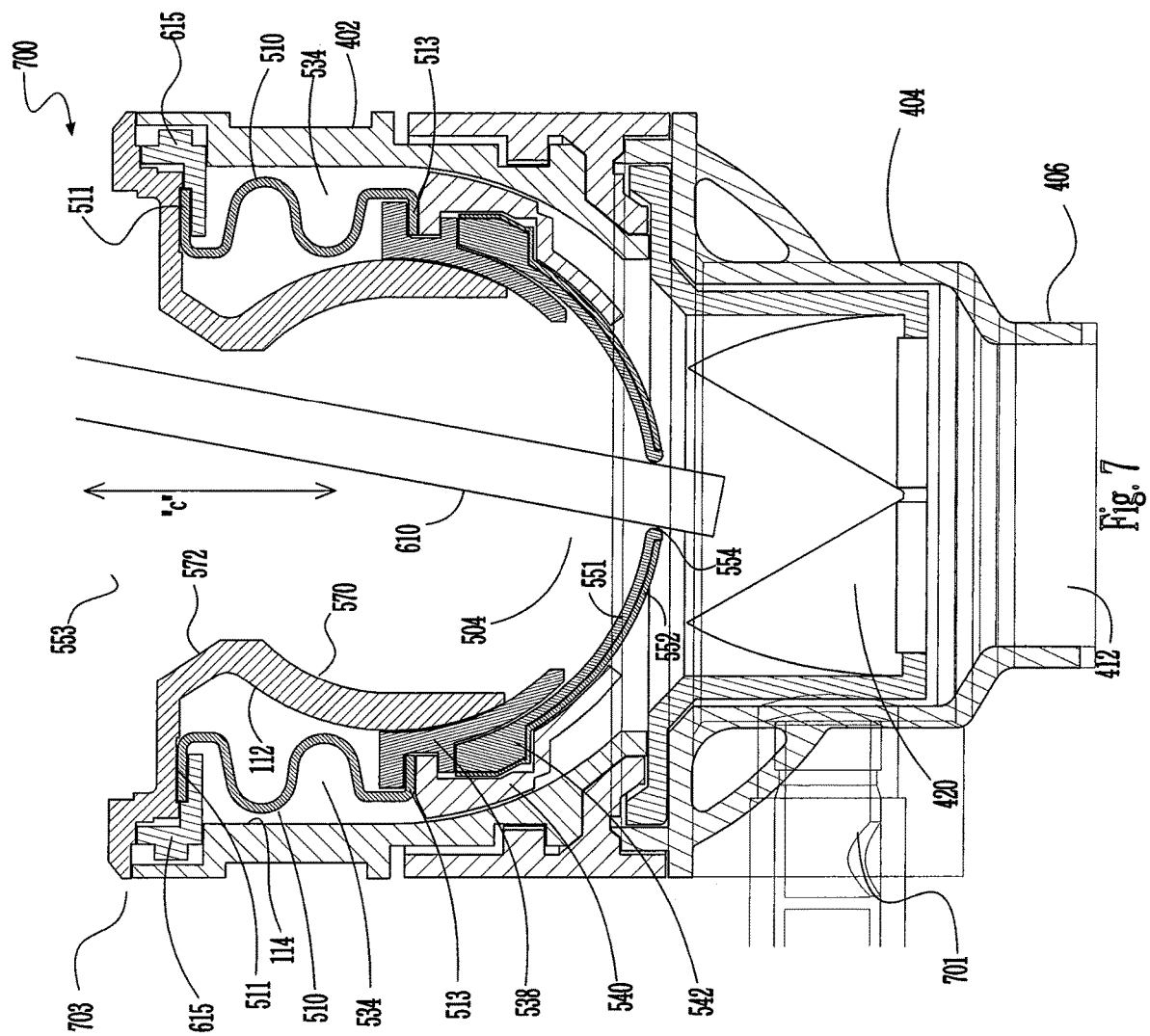
FIG. 7 is a side cross-sectional view of the bellows and gimbal mount connected to the cannula assembly of FIG. 4, in accordance with an embodiment of the present disclosure.

Referring to FIG. 6, a side cross-sectional view 600 of the bellows 510 and gimbal mount 504 positioned within the upper cannula housing 402, in accordance with an embodiment of the present disclosure is presented. Referring to FIG. 7, a side cross-sectional view 700 of the bellows 510 and gimbal mount 504 connected to the upper cannula housing 402, in accordance with an embodiment of the present disclosure is presented.

Referring to both FIGS. 6 and 7, gimbal mount 504 is accommodated within an annular space 534 defined between inner and outer walls 112, 114 of proximal housing component 106 (see FIG. 3). Gimbal mount 504 is mounted in a manner that permits angulation of the gimbal mount 504 relative to seal axis "c." Specifically, gimbal mount 504 is free to angulate about an axis or center of rotation "c" through a range of motion defined within the confines of annular space 534. An annular stop (not shown) may extend within annular space 534. Annular stop may be positioned to limit the degree of angulation of gimbal mount 504 if desired. The range of movement of gimbal mount 504 will be discussed in greater detail hereinbelow. Annular space 534 includes bellows 510 for maintaining the gimbal mount 504 in a biased position (i.e., at an angle with respect to axis "c") when an instrument "i" (see FIGS. 21A and 22A) is inserted through opening 553. It is noted that the top portion of the upper cannula housing 402 includes angled portions 570 for enabling angular insertion of instruments "i," see FIGS. 21A and 22A. The angulation allows for easier insertion and manipulation of instruments inserted therethrough.

It is contemplated that the bellows 510 is some type of flexible or semi-rigid rubber structure for re-positioning the gimbal mount 504 in a substantially central position with respect to axis "c," when the surgical instrument 610 is removed from the opening 553. Bellows 510 may extend around the circumference or periphery of the top portion of the gimbal mount 504.

The gimbal mount 504 and bellows 510 rest within the upper cannula housing 402, such that the first end 511 of the bellows 510 extends toward the proximal end 603 of the upper cannula housing 402, whereas the aperture 554 of the gimbal mount 504 rests on the distal end 601 of the upper cannula housing 402. Additionally, surgical instrument 610 is shown inserted through the opening 553 and a portion of the surgical instrument 610 exiting the aperture 554 to enter into, for example, a body cavity of a patient.

As illustrated, the first end 511 of the bellows 510 is attached or connected to a proximal wall 615 of the upper cannula housing 402. The second end 513 of the bellows 510 seals the radially outer part of the gimbal mount 504 to inhibit leakage, thus eliminating the need for an interface seal or skirt seal, as described above with reference to FIGS. 1-3. Thus, bellows 510 provides some self-centering that pushes or readjusts the gimbal mount 504 toward a centered, unbiased position. Therefore, the first end 511 of the bellows 510 connects to a top wall or top portion or top segment or distal portion/segment of the upper cannula housing 402 (as opposed to the side walls of the upper cannula housing 402). In a preferred arrangement, gimbal mount 504 may angulate through an angle inclusive of about 30°, more preferably about 22.5° relative to cannula housing axis "c."

In operation, the instrument 610 passes into the lower cannula housing 404 passing through duckbill valve 420 (see FIG. 7) and cannula sleeve 406 into the body cavity. In other words, the instrument 610 moves from the proximal end 703 toward the distal end 701 of the surgical access system. Once the instrument 610 is disposed within aperture 554, gimbal mount 504 swivels with respect to the upper and lower cannula housings 402, 404 as the instrument 610 is manipulated. The gimbal mount 504 is free to swivel relative to upper cannula housing 402, while maintaining the seal around the gimbal mount 504. Preferably, the seal member 542 includes resilient material and fabric material, which resists deformation of aperture 554, as well as tearing of seal member 542.

Figure 8:
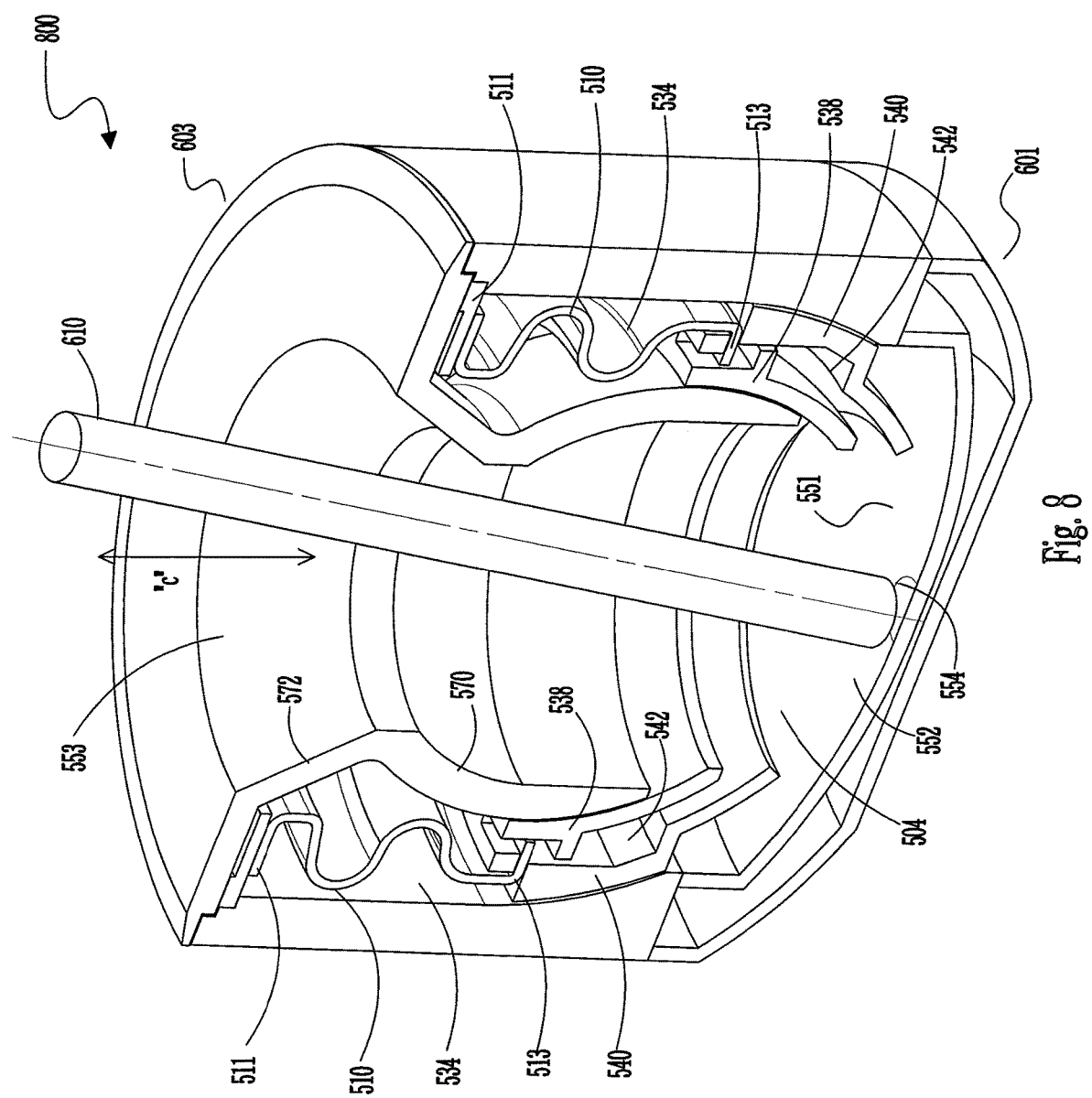
FIG. 8 is a perspective, side cross-sectional view of FIG. 7, further illustrating a surgical instrument inserted therethrough, in accordance with another embodiment of the present disclosure.

Referring to FIG. 8, a perspective, side cross-sectional view 800 of FIG. 7, further illustrating the surgical instrument 610 inserted therethrough is presented. FIG. 8 clearly illustrates the surgical instrument 610 inserted through the opening 553 and engaging the arcuate surface 572, and passing through the gimbal mount 504 toward the aperture 554.

Figure 9A:
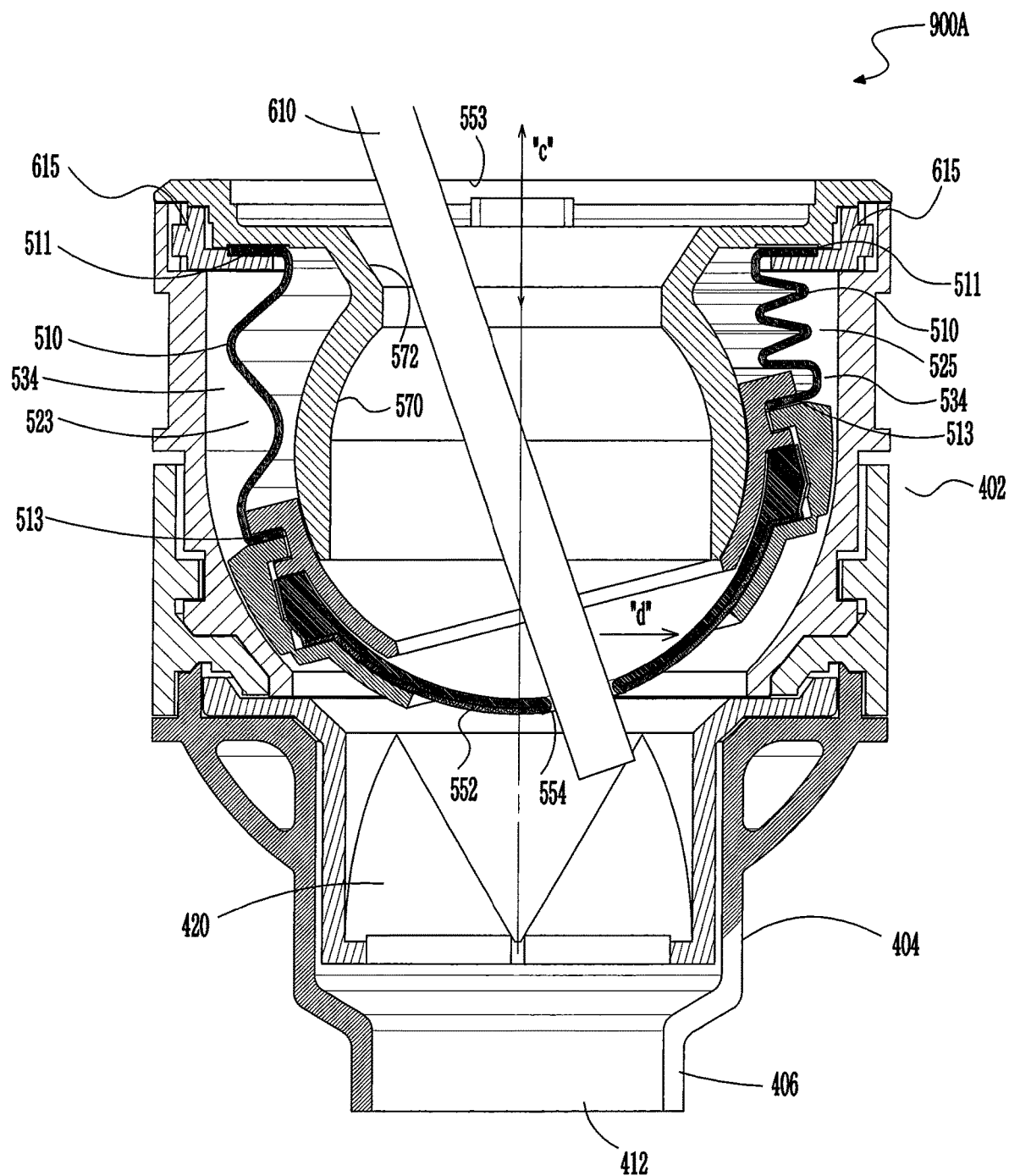
FIGS. 9A and 9B are side, cross-sectional views of the gimbal mount where the bellows is contracted on one end and expanded of the other end when a surgical instrument passes therethrough, in accordance with an embodiment of the present disclosure.
Figure 9B:
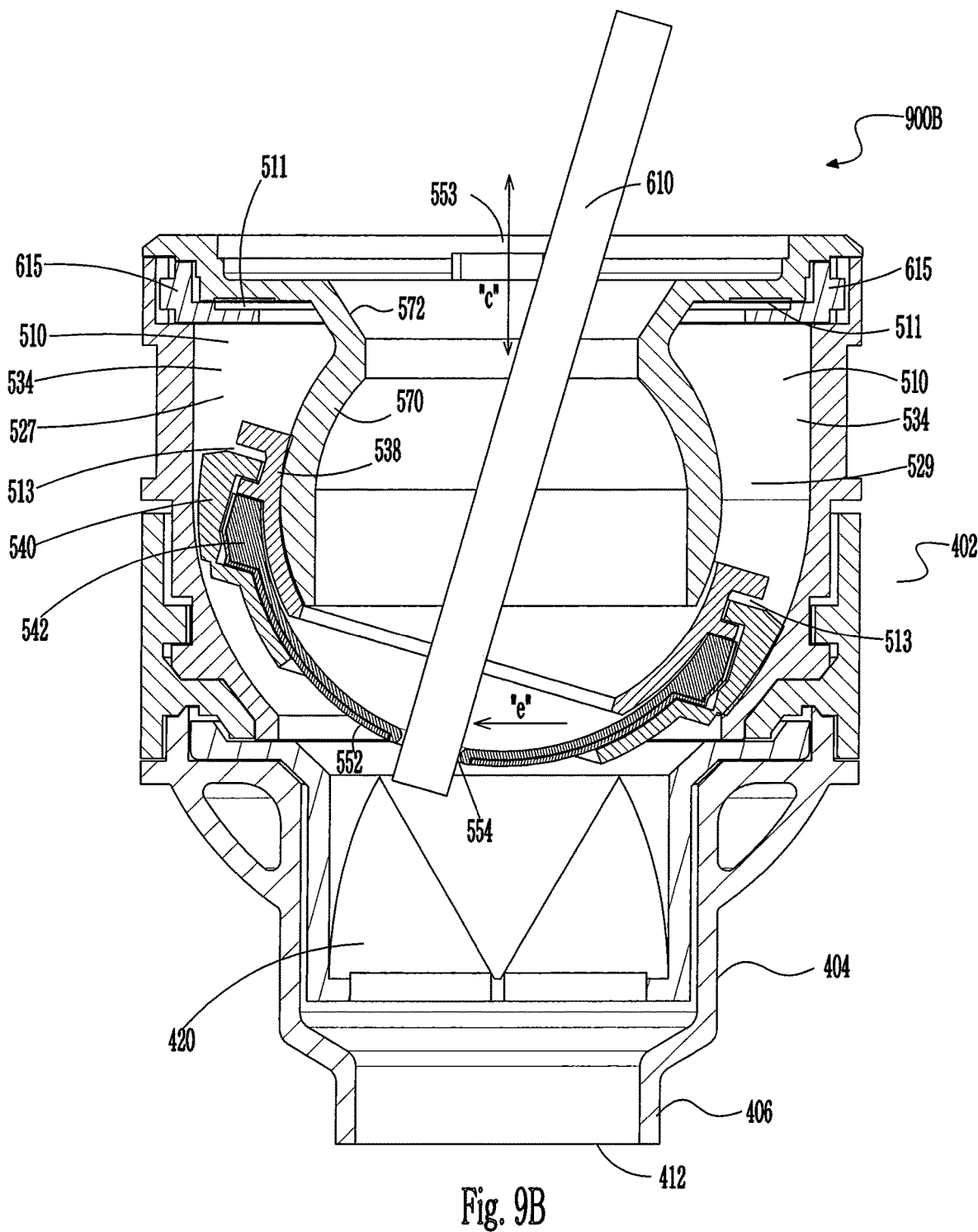
Figure 12:
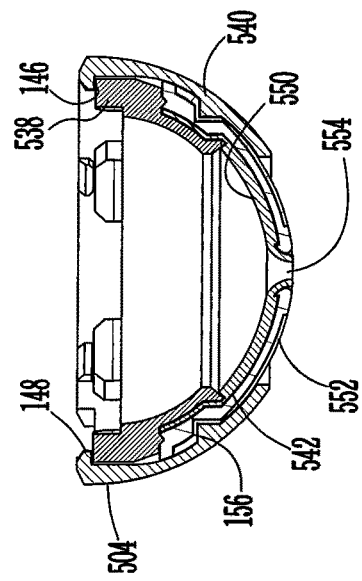
FIGS. 12-13 are cross-sectional views of the gimbal mount, in accordance with the embodiments of FIGS. 5-9B.
Figure 13:
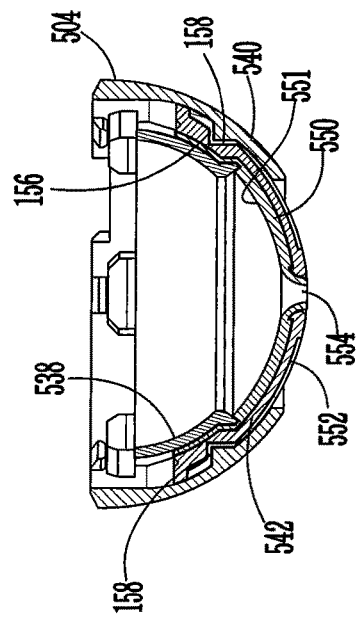
Figure 10:
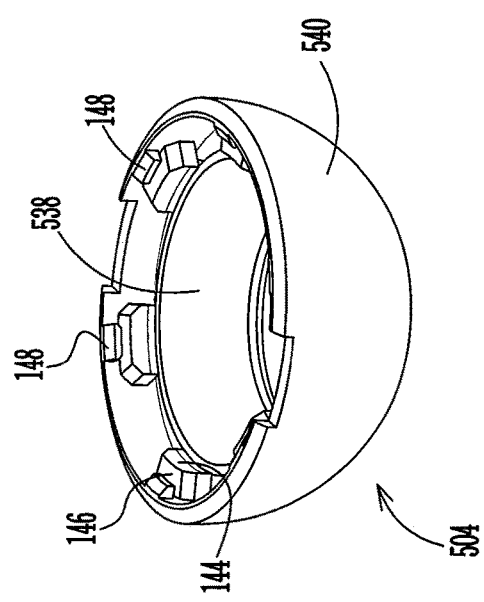
FIGS. 10-11 are top and bottom perspective views of the gimbal mount of the seal assembly of FIGS. 5-9B, in accordance with an embodiment of the present disclosure.

Referring to FIGS. 9A and 9B, side views 900A, 900B of the gimbal mount 504 where the bellows 510 is contracted on one end and expanded of the other end when the surgical instrument 610 passes therethrough, in accordance with an embodiment of the present disclosure are presented.

As shown in FIG. 9A, gimbal mount 504 has been swiveled in a direction "d." For example, the surgical instrument 610 is inserted through opening 553 of the upper cannula housing 402 to reposition the gimbal mount 504 to the right. The right side of the bellows 510 is in a compressed configuration 525, whereas the left side of the bellows 510 is in a stretched configuration 523. As shown in FIG. 9B, gimbal mount 504 has been swiveled in a direction "e." For example, the surgical instrument 610 is inserted through opening 553 of the upper cannula housing 402 to reposition the gimbal mount 504 to the left. The left side of the bellows 510 is in a compressed configuration 527, whereas the right side of the bellows 510 is in a stretched configuration 529. Additionally, energy is stored on the compressed side of the bellows 510 that is used to center the gimbal mount 504 when the instrument 610 is removed.

After the surgical instrument 610 has been removed from the cannula assembly 200, bellows 510 enables gimbal mount 504 to move back to its original position (i.e., an unbiased or neutral position). The unbiased position is one where the gimbal mount 504 is centered with respect to axis "c." Stated differently, bellows 510 may force or propel or guide gimbal mount 504 to return to a position co-axial with the cannula assembly 200. Thus, displacement of gimbal mount 504 from a substantially central position is negated by bellows 510, once the surgical instrument 610 has been removed. Bellows 510 may be moved or adjusted or displaced within the annular space 534 in order to re-position the gimbal mount 504 to a substantially central position with respect to the cannula assembly 200.

Moreover, to reiterate, in FIGS. 9A and 9B, bellows 510 is attached or connected or secured to a proximal wall 615 (or distal end or distal portion/segment or top wall) of the upper cannula housing 402, thus enabling bellows 510 to freely move within the annular space 534 without any hindrances from any other components. As a result, this configuration seals the radially outward part of the gimbal mount 504 to the upper cannula housing 402 to inhibit leakage. Additionally, it also eliminates the need for an interface seal or skirt seal (as described above with reference to FIG. 3). The vertical structure of the bellows 510 also provides self-centering that pushes the gimbal mount 504 toward a center position with respect to axis "c." Moreover, the width (and overall size of the system) of the upper cannula housing 402 may be reduced by constructing the bellows 510 as a vertical structure that connects to the top wall of the upper cannula housing 402 because less space is required on the sides of the upper cannula housing 402. Thus, the space between the side walls of the upper cannula housing 402 and the outer surface of the gimbal mount 504 need not be adapted and dimensioned to accommodate the size of the bellows 510, as the bellows 510 extends adjacent the outer surface of the gimbal mount 504, vertically toward the top wall of the upper cannula housing 402.

Referring now to FIGS. 10-14, in conjunction with FIGS. 5-9B, the components of the gimbal mount 504 will be discussed in further detail. Gimbal mount 504 includes first and second gimbal housings 538, 540 and resilient seal member 542 (see FIG. 12), which is mounted between the housings 538, 540. In a preferred arrangement, first and second gimbal housings 538, 540 and seal member 542 each define a general hemispherical configuration as shown. First gimbal housing 538 is preferably seated within second gimbal housing 540 and secured to the second gimbal housing 540 through a snap fit connection or the like. Preferably, first gimbal housing 538 includes a plurality of mounting legs 144 radially spaced about the outer periphery of the housing component. Legs 144 define locking surfaces 146 which extend in general transverse relation to the axis "b" of seal assembly 100 (see FIG. 3).

Similarly, second gimbal housing 540 includes a plurality of corresponding locking detents 148 spaced about the interior of the housing 540. Upon insertion of first gimbal housing 538 within second gimbal housing 540, mounting legs 144 slide along locking detents 148 whereby upon clearing the detents 148, locking surfaces 146 of the mounting legs 146 securely engage the locking detents 148 to fix first gimbal housing 538 within second gimbal housing 540 and securing resilient seal member 542 between the components in sandwiched relation. As appreciated, first gimbal housing 538 may be sufficiently resilient to deflect upon insertion to permit mounting legs 144 to clear locking detents 148 and return to their initial position to engage the detents 148.

As mentioned hereinabove, seal member 542 of gimbal mount 504 is secured in interposed relation between first and second gimbal housings 538, 540. Seal member 542 preferably comprises a resilient center material (e.g., polyisoprene or natural rubber) with first and second layers of fabric 550, 552 impregnated on the respective proximal and distal surfaces of the resilient center material. Fabric may be of any suitable fabric for example, a SPANDEX material containing about 20% LYCRA and about 80% NYLON available from Milliken. Seal member 542 defines central aperture 554 for sealed reception of a surgical instrument.

In a preferred arrangement, first layer 550 is arranged to extend or overlap into aperture 554. In this manner, the fabric (which is stronger relative to the resilient material) is positioned to engage the surgical instrument upon passage through aperture 554 of seal member 542 thereby protecting the resilient material defining the aperture. This advantageously minimizes the potential of piercing, penetrating or tearing of the resilient material by the instrument. Alternatively, an additional layer of fabric 551 on the proximal surface of seal member 542 may be superposed and arranged to drape within aperture 554. Seal member 542 includes an annular depression 156 (see FIG. 12) on its distal surface, i.e., within second layer 552 of fabric. Depression 156 receives ledge 158 (see FIG. 13) of second gimbal housing 540 to facilitate fixation of seal member 542 between first and second gimbal housings 538, 540.

Figure 11:
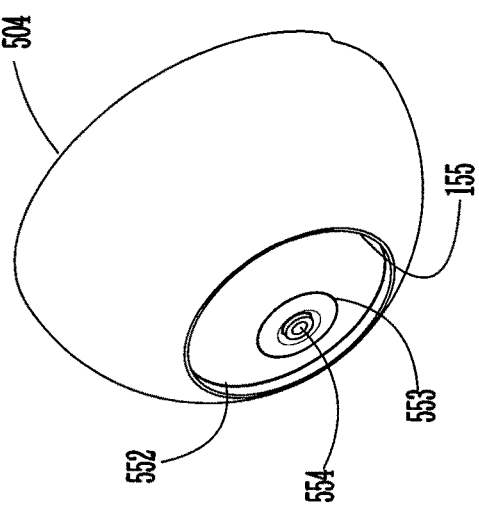
Figure 14:
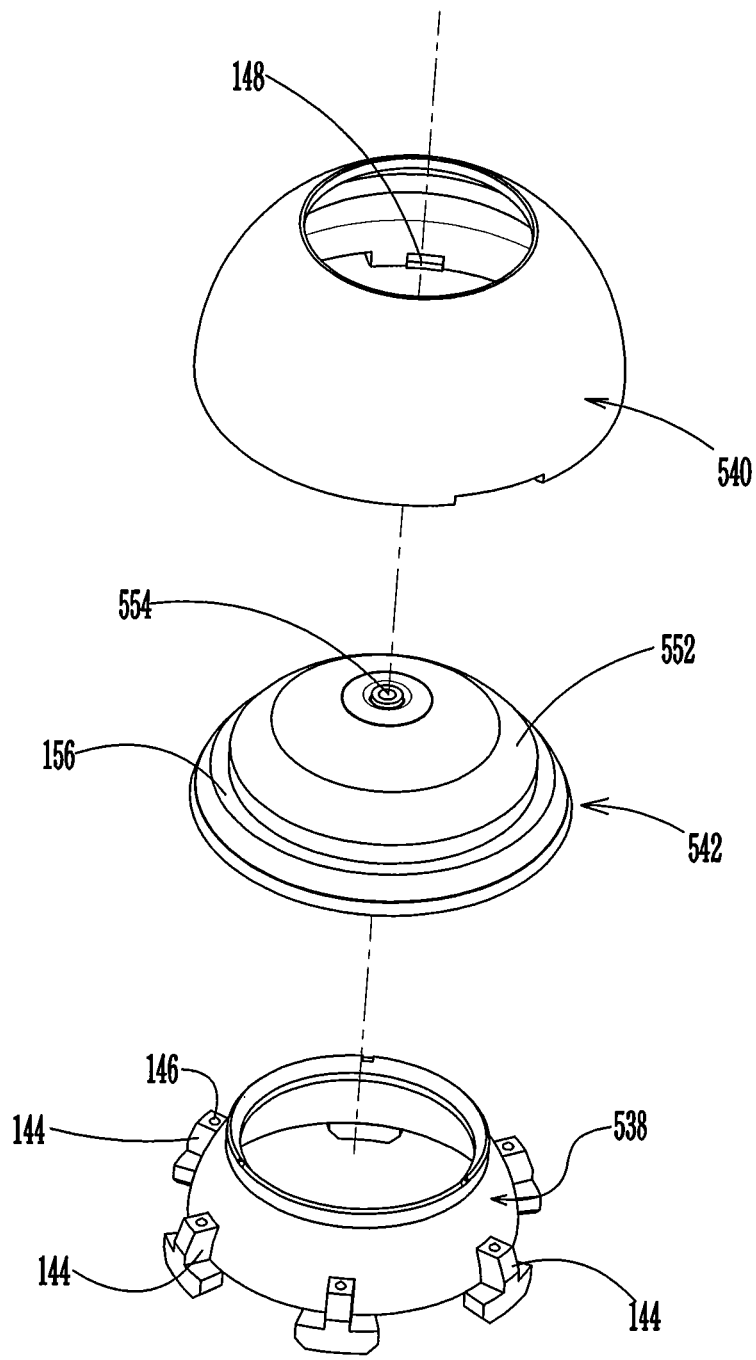
FIG. 14 is a perspective view illustrating the components of the gimbal mount, in accordance with the embodiments of FIGS. 5-9B.

Although seal member 542 is disclosed as an impregnated fabric arrangement, it is appreciated that other seal types may be used and still achieve the objectives of the present disclosure. Further, FIG. 11 illustrates annular depressions 553, 155 which have been pressed by a molding tool into layer 553. One or more similar depressions may be pressed into layer 550 to assist positioning of fabric during manufacture of seal member 542.

Figure 17:
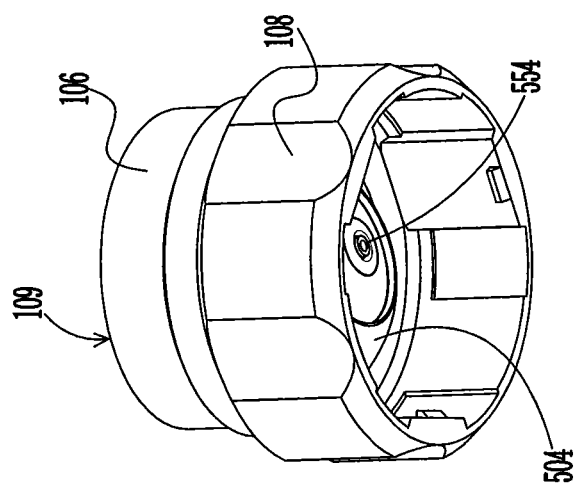
FIGS. 15-17 are perspective views illustrating the range of movement of the gimbal mount within the seal housing, in accordance with the embodiments of FIGS. 5-9B.
Figure 16:
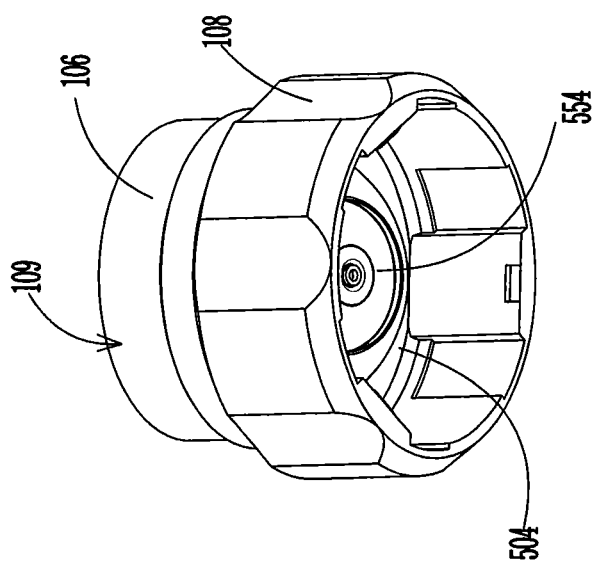
Figure 15:
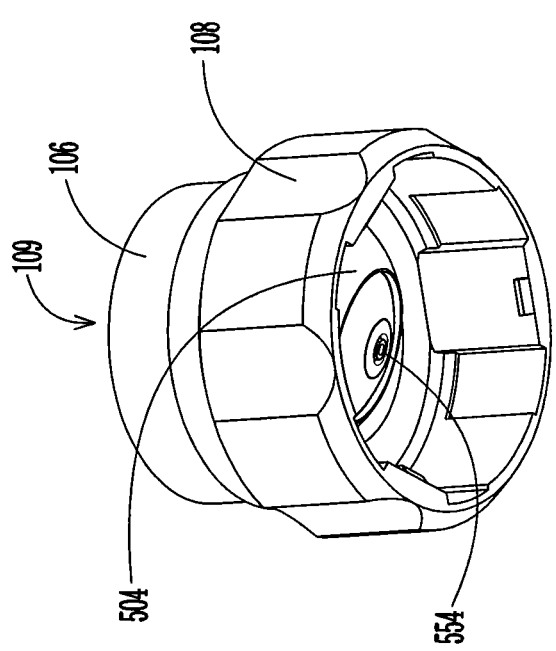

With reference now to FIGS. 15-17, in conjunction with FIGS. 5-9B, gimbal mount 504 is free to move within the annular space 534 defined between inner and outer walls 112, 114 (see FIG. 3) to permit angulation of the instrument relative to the seal axis "b" while still maintaining a seal thereabout. Specifically, gimbal mount 504 is adapted for swiveling movement about a center of rotation "c," which is coincident with the axis of seal assembly 100 (see FIG. 1). In this regard, the axis of the aperture 554 of seal member 542 intersects the axis "b" of the seal assembly 100 during angulation of the instrument. During angulation, gimbal mount 504 is in contact with bellows 510 (see FIGS. 6, 7, 8, 9A, and 9B) attached to a top wall or proximal wall 615 of the upper cannula housing 402. Bellows 510 extends vertically upward substantially adjacent the outer surface of the gimbal mount 504 toward the proximal wall 615. In a preferred arrangement, gimbal mount 504 may angulate or rotate through an angle inclusive of about 25°, more preferably about 22.5° relative to seal axis "b."

Figure 18:
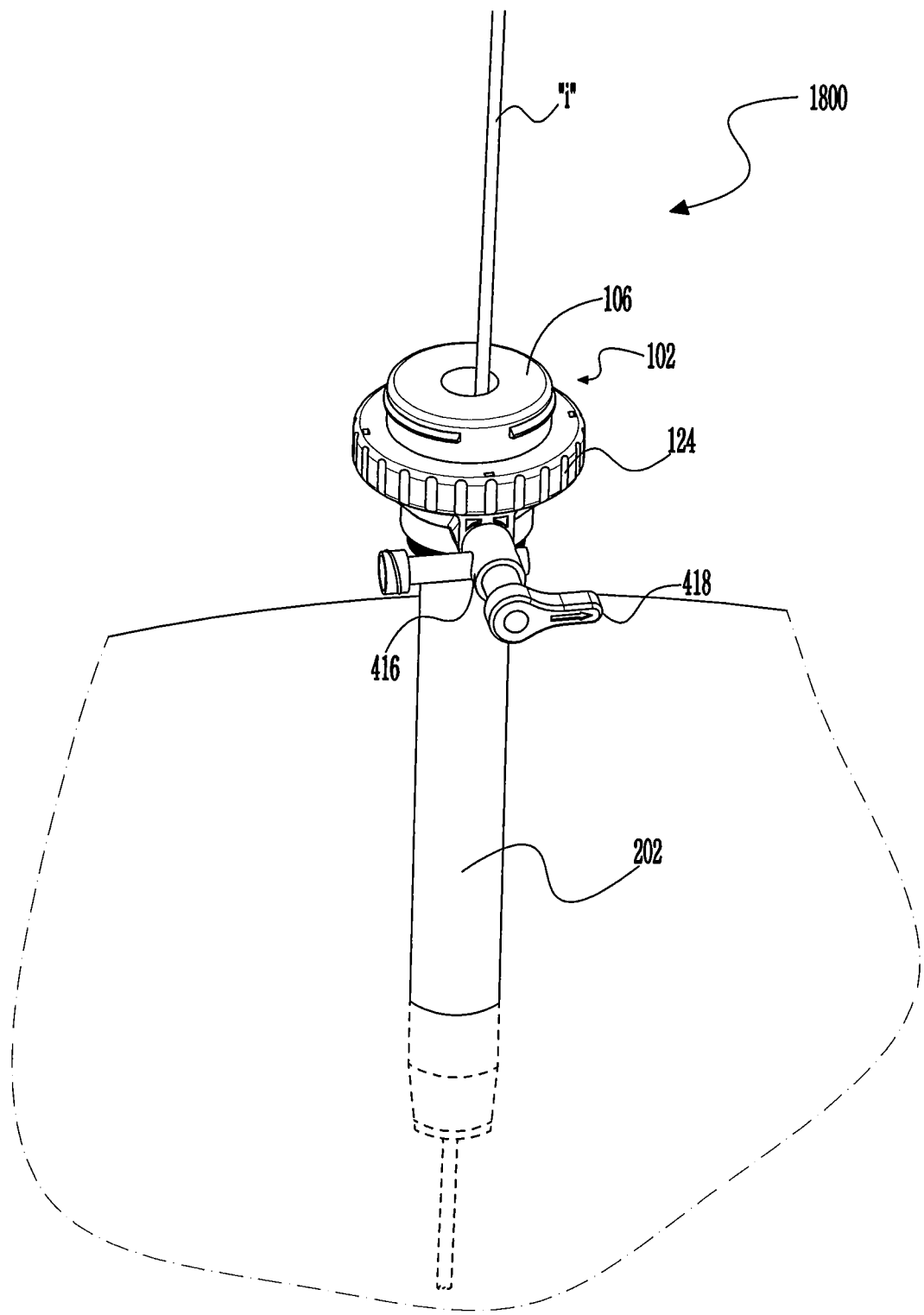
FIG. 18 is a perspective view illustrating the cannula assembly and seal assembly accessing an internal cavity with an instrument introduced therein, in accordance with the embodiments of the present disclosure.

FIG. 18 illustrates a perspective view 1800 of an instrument "i" introduced through the seal assembly 100 connected to the cannula assembly 200. FIGS. 19A-22B illustrate side cross-sectional views of the instrument "i" inserted through the seal assembly 100 connected to the cannula assembly 200.

Referring to FIG. 18, cannula housing 402 may include a port opening and luer fitting 416 positioned within the port opening. Luer fitting 416 is adapted for connection to a supply of insufflation gas and incorporates valve 418 to selectively open and close the passage of the luer fitting 416. Cannula housing 402 further includes duckbill or zero closure valve 420, which tapers distally and inwardly to a sealed configuration. Closure valve 420 defines a slit (not shown), which opens to permit passage of the surgical instrumentation and closes in the absence of the instrumentation. Closure valve 420 is preferably adapted to close upon exposure to the forces exerted by the insufflation gases in the internal cavity. Other zero closure valves are also contemplated, including single or multiple slit valve arrangements, trumpet valves, flapper valves, etc.

Figure 19A:
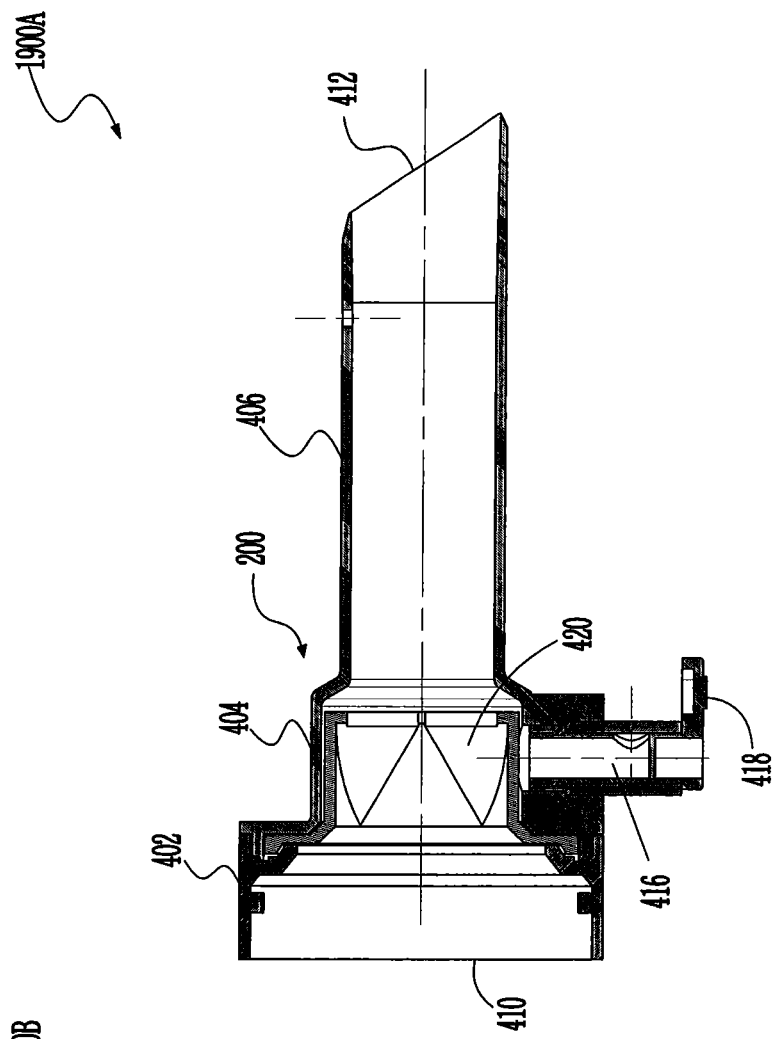
FIG. 19A is a side cross-sectional view of the cannula assembly, in accordance with the embodiments of the present disclosure.
Figure 19B:
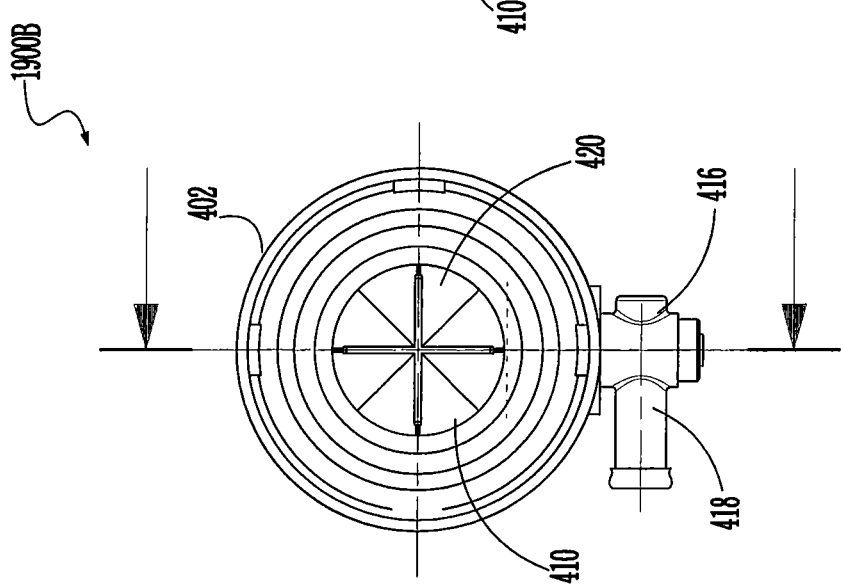
FIG. 19B is a top view of the cannula assembly of FIG. 19A.

FIG. 19A illustrates a side view 1900A of the cannula assembly 200 without the gimbal mount 504 and bellows 510, whereas FIG. 19B illustrates a top view 1900B of the cannula assembly 200. FIG. 20A illustrates a side view 2000A of the cannula assembly 200 incorporating the gimbal mount 504 and the bellows 510, whereas FIG. 20B illustrates a top view 2000B of the cannula assembly 200 incorporating the gimbal mount 504 and the bellows 510.

FIG. 21A is a side view 2100A of the cannula assembly 200 incorporating the gimbal mount 504 and the bellows 510, where surgical instrument 610 has been inserted therethrough and displaced gimbal mount 504 in direction "e." FIG. 21B is a top view of 2100B of the cannula assembly 200 incorporating the gimbal mount 504 and the bellows 510. FIG. 22A is a side view 2200A of the cannula assembly 200 incorporating the gimbal mount 504 and the bellows 510, where surgical instrument 610 has been inserted therethrough and displaced gimbal mount 504 in direction "d."

FIG. 22B is a top view of 2200B of the cannula assembly 200 incorporating the gimbal mount 504 and the bellows 510.

In operation or use, as the instrument 610 is moved up and down axes "d" or "e," bellows 510 maintains the instrument 610 in its biased position, as desired by the user. The biased position is an off-center positioned with respect to axis "c," as illustrated in FIGS. 5-9B. In the biased position, the bellows 510 expands and contracts on either side of the cannula assembly 200. Energy is stored on the compressed side of the bellows 510 that is used to center the gimbal mount 504 when the instrument 610 is removed. When the instrument 610 is removed from the seal assembly 100 and cannula assembly 200, bellows 510 re-positions the gimbal mount 504 back to its centered and unbiased position. The unbiased position is a substantially central position with respect to axis "c." Thus, bellows 510 acts to negate the displacement caused by the insertion of one or more surgical instruments through the cannula assembly 200. Stated differently, gimbal mount 504 is re-positioned to its initial unbiased position, where the gimbal mount 504 is coaxial with axis "c" defined by the cannula assembly 200. Additionally, bellows 510 seals the gimbal mount 504 to the seal assembly 100 and allow for rotation or swiveling of the gimbal mount 504.

Therefore, in summary, with reference to FIGS. 5-22B, bellows 510 is attached or connected or secured to a proximal wall 615 (or distal end or distal portion/segment or top wall) of the upper cannula housing 402, thus enabling bellows 510 to freely move within the annular space 534 without any hindrances from any other components. As a result, this configuration seals the radially outward part of the gimbal mount 504 to the upper cannula housing 402 to inhibit leakage. Additionally, it also eliminates the need for an interface seal or skirt seal (as described above with reference to FIG. 3). The vertical structure of the bellows 510 also provides self-centering that pushes the gimbal mount 504 toward a center position with respect to axis "c." Moreover, the width (and overall size of the system) of the upper cannula housing 402 may be reduced by constructing the bellows 510 as a vertical structure that connects to the top wall of the upper cannula housing 402 because less space is required on the sides of the upper cannula housing 402. Thus, the space between the side walls of the upper cannula housing 402 and the outer surface of the gimbal mount 504 need not be adapted and dimensioned to accommodate the size of the bellows 510, as the bellows 510 extends adjacent the outer surface of the gimbal mount 504, vertically toward the top wall of the upper cannula housing 402.

Figure 23:
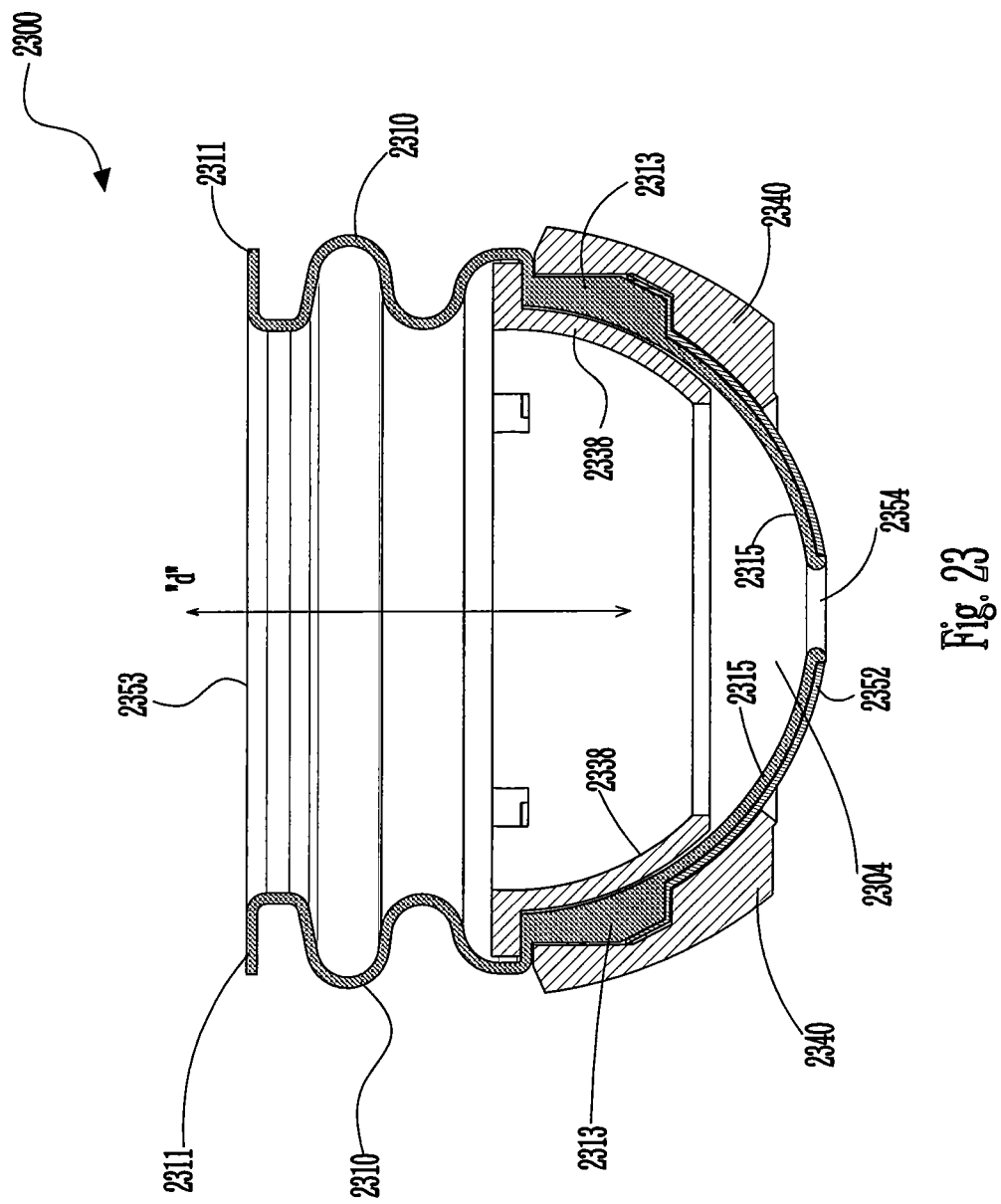
FIG. 23 is a side cross-sectional view of the bellows attached to the gimbal mount, where the bellows and gimbal mount are one integral unit, in accordance with an embodiment of the present disclosure.

Referring to FIG. 23, a side cross-sectional view 2300 of the bellows 2310 attached to the gimbal mount 2304, where the bellows 2310 and gimbal mount 2304 are one integral unit, in accordance with an embodiment of the present disclosure is presented.

Gimbal mount 2304 includes first and second gimbal housings 2338, 2340 and bellows 2310 has a distal portion which extends between the housings 2338, 2340. In a preferred arrangement, first and second gimbal housings 2338, 2340 each define a substantially hemispherical configuration. However, one skilled in the art may contemplate a gimbal mount 2304 defining a substantially parabolic configuration. First gimbal housing 2338 is preferably seated within second gimbal housing 2340 and secured to the second gimbal housing 2340 through a snap fit connection or the like.

Bellows 2310 defines central aperture 2354 for sealed reception of a surgical instrument. In a preferred arrangement, first layer 2315 is arranged to extend or overlap into aperture 2354. In this manner, the fabric (which is stronger relative to the resilient material) is positioned to engage the surgical instrument upon passage through aperture 2354, thereby protecting the resilient material defining the aperture 2354. Moreover, the distal end 2313 of the bellows 2310 interacts with fabric 2352 to stabilize the distalmost end 2313 to create the aperture 2354. This advantageously minimizes the potential of piercing, penetrating or tearing of the resilient material by the instrument.

Bellows 2310 includes a proximal end 2311 and a distal end 2313. Bellows 2310 extends through the housings 2338, 2340 and up to the aperture 2354. Bellows 2310 also includes an opening 2353 for receiving surgical instrumentation, as will be discussed in further detail below. Gimbal mount 2304 is free to move and is in cooperation with bellows 2310 to permit angulation of the instrument relative to the seal axis "d," while still maintaining a seal thereabout. Therefore, bellows 2310 is one single integral unit that extends between housing components 2338, 2340 of the gimbal mount 2304.

Figure 24:
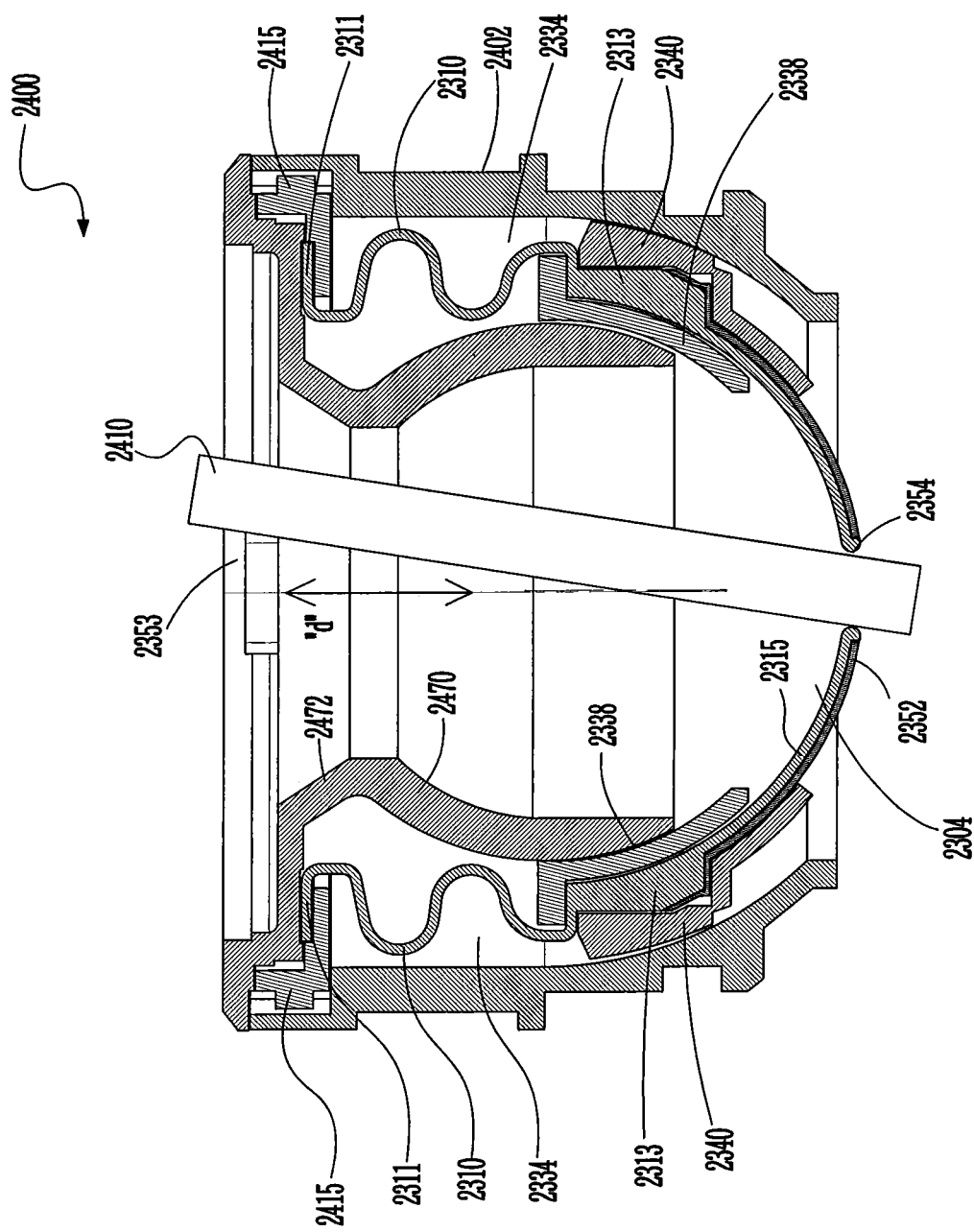
FIG. 24 is a side cross-sectional view of the bellows and gimbal mount, where the bellows and gimbal mount are one integral unit, and positioned within the seal housing, in accordance with an embodiment of the present disclosure.

Referring to FIG. 24, a side cross-sectional view 2400 of the bellows 2310 and gimbal mount 2304, where the bellows 2310 and gimbal mount 2304 are one integral unit, and positioned within the upper cannula housing 2402, in accordance with an embodiment of the present disclosure is presented.

Gimbal mount 2304 is accommodated within an annular space 2334. Gimbal mount 2304 is mounted in a manner that permits angulation of the gimbal mount 2304 relative to seal axis "d." Specifically, gimbal mount 2304 is free to angulate about an axis or center of rotation "d" through a range of motion defined within the confines of annular space 2334. An annular stop (not shown) may extend within annular space 2334. Annular stop may be positioned to limit the degree of angulation of gimbal mount 2304 if desired. Annular space 2334 includes bellows 2310 for maintaining the gimbal mount 2304 in a biased position when an instrument 2410 is inserted through opening 2353. It is noted that the top portion of the upper cannula housing 2402 include angled portions 2470 for enabling angular insertion of instruments 2410. The angulation allows for easier insertion and manipulation of instruments inserted therethrough.

It is contemplated that the bellows 2310 is some type of flexible or semi-rigid rubber structure for re-positioning the gimbal mount 2304 in a substantially central position with respect to axis "d," when the surgical instrument 2410 is removed from the opening 2353.

As illustrated, the first end 2311 of the bellows 2310 is attached or connected to a proximal wall 2415 of the upper cannula housing 2402. The second end 2313 of the bellows 2310 seals the radially outer part of the gimbal mount 2304 to inhibit leakage, thus eliminating the need for an interface seal or skirt seal, as described above with reference to FIGS. 1-3. Thus, bellows 2310 provides some self-centering force that pushes or readjusts the gimbal mount 2304 toward a centered, unbiased position. Therefore, the first end 2311 of the bellows 2310 connects to a top wall or top portion or top segment or distal portion/segment of the upper cannula housing 2402 (as opposed to the side walls of the upper cannula housing 2402). In a preferred arrangement, gimbal mount 2304 may angulate through an angle inclusive of about 30°, more preferably about 22.5° relative to upper cannula housing axis "d." FIG. 24 clearly illustrates the surgical instrument 2410 inserted through the opening 2353 and engaging the arcuate surface 2472, and passing through the gimbal mount 2304 toward the aperture 2354. The distal end 2313 of the bellows 2310 interacts with fabric 2352 to stabilize the distalmost end 2313 to create the aperture 2354.

Figure 25A:
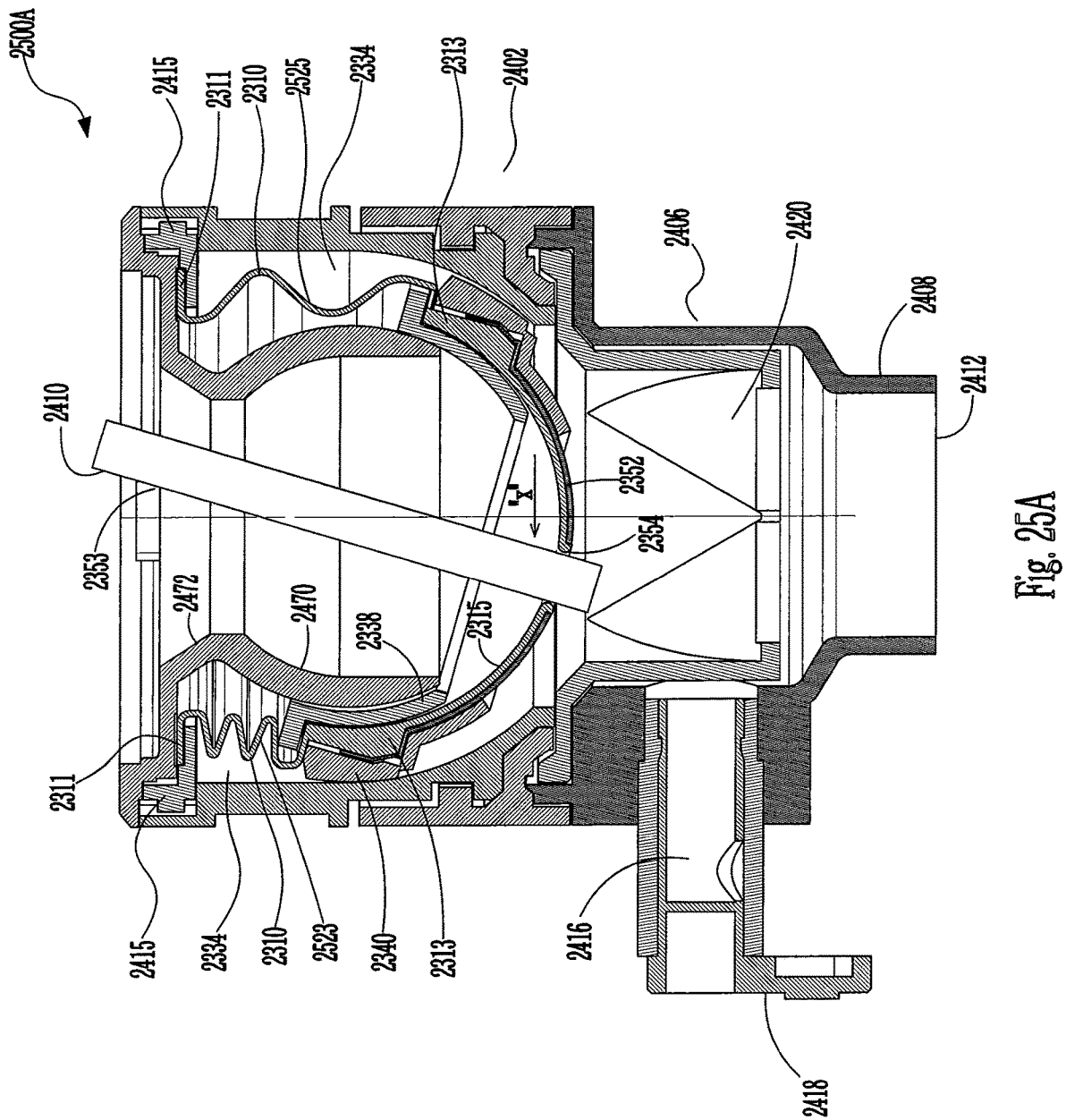
FIGS. 25A and 25B are side views of the gimbal mount where the bellows is contracted on one end and expanded of the other end when a surgical instrument passes therethrough, where the bellows and the gimbal mount are one integral unit, in accordance with an embodiment of the present disclosure.
Figure 25B:
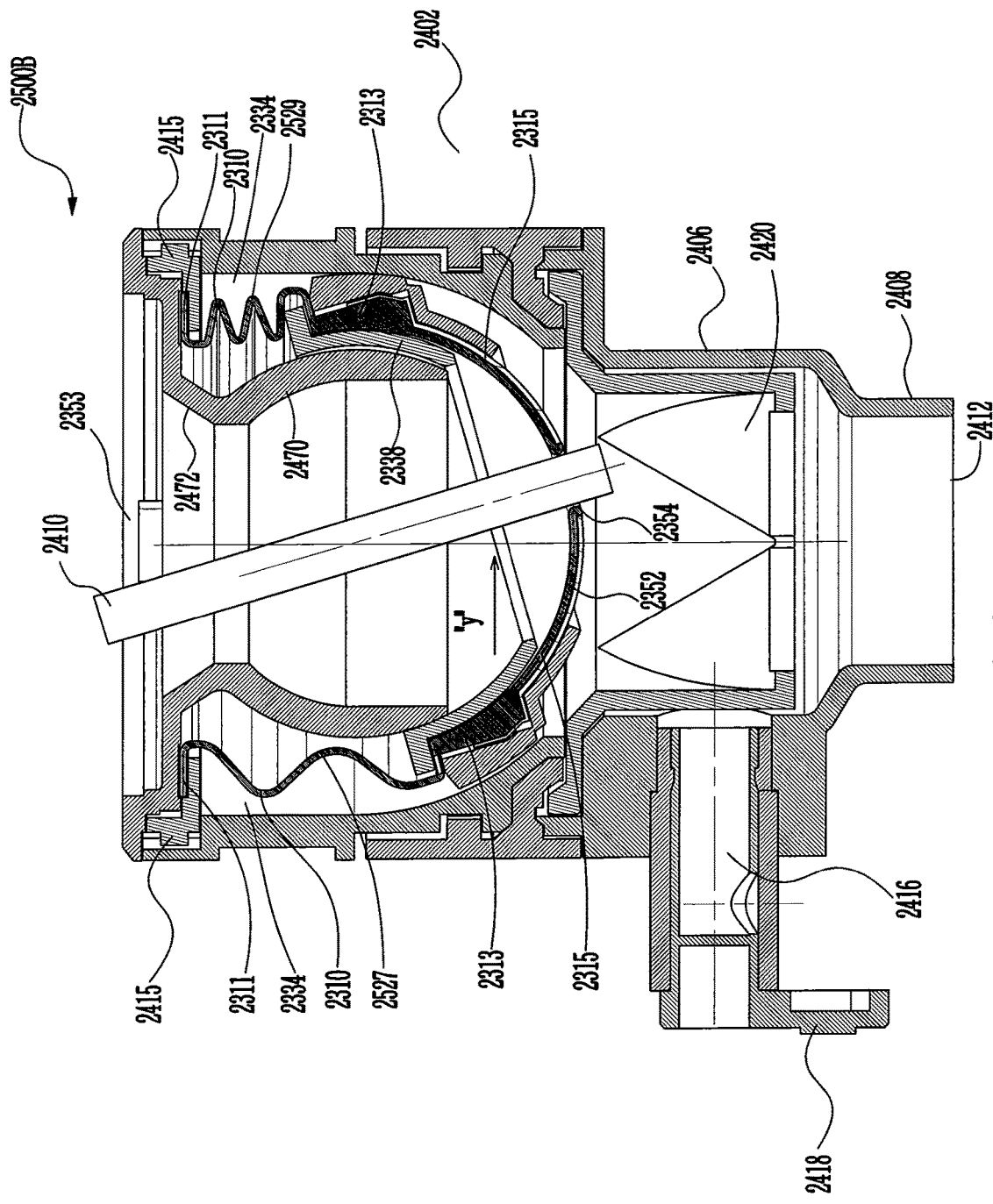

Referring to FIGS. 25A and 25B, side views 2500A, 2500B of the gimbal mount 2304 where the bellows 2310 is contracted on one end and expanded of the other end when a surgical instrument 2410 passes therethrough are presented, where the bellows 2310 and the gimbal mount 2304 are one integral unit, in accordance with an embodiment of the present disclosure.

As shown in FIG. 25A, gimbal mount 2304 has been swiveled in a direction "x." For example, the surgical instrument 2410 is inserted through opening 2353 of the upper cannula housing 2402 to swivel the gimbal mount 504 to the left. As shown in FIG. 25B, gimbal mount 2304 has been swiveled in a direction "y." For example, the surgical instrument 2410 is inserted through opening 2353 of the upper cannula housing 2402 to swivel the gimbal mount 504 to the right. In FIG. 25A, it is noted that the left side of the bellows 2310 is in a compressed configuration 2523, whereas the right side of the bellows 2310 is in a stretched configuration 2525. In FIG. 25B, it is noted that the right side of the bellows 2310 is in a compressed configuration 2529, whereas the right side of the bellows 2310 is in a stretched configuration 2527. Additionally, energy is stored on the compressed side of the bellows 2310 that is used to center the gimbal mount 2304 when the instrument 2410 is removed.

After the surgical instrument 2410 has been removed from the upper cannula housing 2402, bellows 2310 enables gimbal mount 2304 to move back to its original position (i.e., an unbiased position). The unbiased position is one where the gimbal mount 2304 is centered with respect to axis "d." Stated differently, bellows 2310 may force or propel or guide gimbal mount 2304 to return to a position co-axial with the upper cannula housing 2402. Thus, displacement of gimbal mount 2304 from a substantially central position is negated by bellows 2310, once the surgical instrument 2410 has been removed. Bellows 2310 may be moved or adjusted or displaced within the annular space 2334 in order to re-position the gimbal mount 2304 to a substantially central position with respect to the upper cannula housing 2402. Moreover, the distal end 2313 of the bellows 2310 is configured to aid the movement of the gimbal mount 2304 since the distal end 2313 of the bellows 2310 is sandwiched between the first and second gimbal housings 2338, 2340, and extends distally up to the central aperture 2354.

Moreover, bellows 2310 is attached or connected or secured to a proximal wall 2415 (or distal end or distal portion/segment or top wall) of the upper cannula housing 2402, thus enabling the bellows 2310 to freely move within the annular space 2334 without any hindrances from any other components. As a result, this configuration seals the radially outward part of the gimbal mount 2304 to the upper cannula housing 2402 to inhibit leakage. Additionally, it also eliminates the need for an interface seal. The vertical structure of the bellows 2310 also provides self-centering that pushes the gimbal mount 2304 toward a center position with respect to axis "d." Moreover, the width (and overall size of the system) of the upper cannula housing 2402 may be reduced by constructing the bellows 2310 as a vertical structure that connects to the top wall of the upper cannula housing 2402 because less space is required on the sides of the upper cannula housing 2402. Thus, the space between the side walls and the outer surface of the gimbal mount 2304 need not be adapted and dimensioned to accommodate the size of the bellows 2310, as the bellows 2310 extends adjacent the outer surface of the gimbal mount 2304, vertically toward the top wall of the upper cannula housing 2402.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical access device comprising:
   a seal assembly including a seal housing and a gimbal assembly disposed within the seal housing, the seal housing defining a central longitudinal axis and having a longitudinal passage for receiving at least one surgical object therethrough, the gimbal assembly adapted for angular movement relative to the central longitudinal axis; and
   a bellows extending between the seal housing and the gimbal assembly, the bellows dimensioned and adapted to establish a biasing relationship with the gimbal assembly such that the bellows biases the gimbal assembly to align with the central longitudinal axis of the seal housing, wherein the seal housing includes an extension portion disposed between the bellows and the longitudinal passage and the extension portion is hemispherical.

2. The surgical access device of claim 1, wherein a proximal end of the bellows is attached to a proximal wall of the seal housing.

3. The surgical access device of claim 1, wherein the gimbal assembly includes a first gimbal housing and a second gimbal housing, the seal member being secured between the first gimbal housing and the second gimbal housing.

4. The surgical access device of claim 1, wherein the gimbal assembly includes a first gimbal housing and a second gimbal housing, a distal end of the bellows being secured between the first gimbal housing and the second gimbal housing.

5. The surgical access device of claim 1, wherein the gimbal assembly includes a first gimbal housing and a second gimbal housing, the first gimbal housing being seated within the second gimbal housing.

6. The surgical access device of claim 1, wherein an outer surface of the gimbal assembly is configured to travel along an inner surface of the seal housing.

7. The surgical access device of claim 1, wherein the seal assembly includes an upper housing portion and a lower housing portion, the upper housing portion mechanically cooperating with the bellows such that the bellows is circumferentially adjacent the longitudinal passage of the seal housing.

8. The surgical access device of claim 1, wherein the bellows is dimensioned and adapted to inhibit passage of fluids through the seal housing.

9. The surgical access device of claim 1, wherein the bellows extends from a proximal wall of the seal housing parallel to the central longitudinal axis.

10. The surgical access device of claim 1, wherein a proximal end of the bellows is vertically spaced from a distal end of the bellows.

11. The surgical access device of claim 1, wherein one side of the bellows expands and another side of the bellows contracts as the at least one surgical instrument is inserted through and maneuvered within the longitudinal passage of the seal housing.

12. The surgical access device of claim 1, further including a cannula assembly, the cannula assembly including a cannula housing and a cannula sleeve extending distally from the cannula housing.

13. The surgical access device of claim 12, wherein the seal assembly is disposed in mechanical cooperation with the cannula housing.

14. The surgical access device of claim 1, wherein the extension portion separates the bellows from the at least one surgical object received through the seal housing.

15. The surgical access device of claim 1, wherein the gimbal assembly engages the extension portion.

\* \* \* \* \*